US012766008B2

(12) United States Patent
Harwin et al.

(10) Patent No.: US 12,766,008 B2
(45) Date of Patent: Oct. 20, 2026

(54) LOAD SENSOR BALANCER INSTRUMENTS

(71) Applicant: Howmedica Osteonics Corp., Mahwah, NJ (US)

(72) Inventors: Steven F. Harwin, New York, NY (US); Mohamed Soliman, Fair Lawn, NJ (US); An Chen, Kirkland, WA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 18/984,301

(22) Filed: Dec. 17, 2024

(65) Prior Publication Data

US 2025/0195241 A1 Jun. 19, 2025

Related U.S. Application Data

(60) Continuation of application No. 17/941,416, filed on Sep. 9, 2022, now Pat. No. 12,201,534, which is a division of application No. 16/775,430, filed on Jan. 29, 2020, now abandoned.

(51) Int. Cl.
*A61B 17/02* (2006.01)
*A61F 2/46* (2006.01)

(52) U.S. Cl.
CPC ............ *A61F 2/461* (2013.01); *A61B 17/025* (2013.01); *A61B 2017/0268* (2013.01); *A61F 2002/4666* (2013.01)

(58) Field of Classification Search
CPC ...................... A61B 2017/0268; A61B 17/025
See application file for complete search history.

(56) References Cited

U.S. PATENT DOCUMENTS

| | | | |
|---|---|---|---|
| 4,501,266 | A | 2/1985 | McDaniel |
| 4,566,448 | A | 1/1986 | Rohr, Jr. |
| 4,703,751 | A | 11/1987 | Pohl |
| 5,116,338 | A | 5/1992 | Poggie et al. |
| 5,213,112 | A | 5/1993 | Niwa et al. |
| 5,431,653 | A | 7/1995 | Callaway |
| 5,468,244 | A | 11/1995 | Attfield et al. |
| 5,470,354 | A | 11/1995 | Hershberger et al. |
| 5,540,696 | A | 7/1996 | Booth, Jr. et al. |
| 5,569,260 | A | 10/1996 | Petersen |
| 5,597,379 | A | 1/1997 | Haines et al. |
| 5,669,914 | A | 9/1997 | Eckhoff |
| 5,688,280 | A | 11/1997 | Booth, Jr. et al. |
| 5,733,292 | A | 3/1998 | Gustilo et al. |
| 5,800,438 | A | 9/1998 | Tuke et al. |
| 5,860,980 | A | 1/1999 | Axelson, Jr. et al. |
| 5,911,723 | A | 6/1999 | Ashby et al. |
| 6,022,377 | A | 2/2000 | Nuelle et al. |

(Continued)

*Primary Examiner* — Samuel S Hanna
(74) *Attorney, Agent, or Firm* — Lerner David LLP

(57) ABSTRACT

Disclosed herein are apparatuses and methods for performing joint balancing procedures. The apparatus may have femoral paddle and a tibial paddle attached to a housing. The housing may include a distraction mechanism to vary the space between the femoral paddle and the tibial paddle. The tibial paddle may lie entirely within the femoral paddle in a closed position. A load sensor may be placed in the femoral paddle to measure ligament tension. The apparatus may be inserted into a knee joint and positioned to remain within the knee joint during flexion and extension of the knee without everting a patella.

9 Claims, 15 Drawing Sheets

(56) References Cited

U.S. PATENT DOCUMENTS

| | | | |
|---|---|---|---|
| 6,478,799 | B1 | 11/2002 | Williamson |
| 6,648,896 | B2 | 11/2003 | Overes et al. |
| 6,758,850 | B2 | 7/2004 | Smith et al. |
| 6,770,078 | B2 | 8/2004 | Bonutti |
| 6,859,661 | B2 | 2/2005 | Tuke |
| 7,156,853 | B2 | 1/2007 | Muratsu |
| 7,179,295 | B2 | 2/2007 | Kovacevic |
| 7,309,339 | B2 | 12/2007 | Cusick et al. |
| 7,329,260 | B2 | 2/2008 | Auger et al. |
| 7,381,223 | B2 | 6/2008 | Kovacevic |
| 7,412,897 | B2 | 8/2008 | Crottet et al. |
| 7,442,196 | B2 | 10/2008 | Fisher et al. |
| 7,455,647 | B2 | 11/2008 | Tarabichi |
| 7,470,288 | B2 | 12/2008 | Dietz et al. |
| 7,575,602 | B2 | 8/2009 | Amirouche et al. |
| 7,578,821 | B2 | 8/2009 | Fisher et al. |
| 7,587,945 | B2 | 9/2009 | Crottet et al. |
| 7,591,854 | B2 | 9/2009 | Wasielewski |
| 7,615,055 | B2 | 11/2009 | DiSilvestro |
| 7,632,283 | B2 | 12/2009 | Heldreth |
| 7,635,369 | B2 | 12/2009 | Cinquin et al. |
| 7,651,500 | B2 | 1/2010 | Supper et al. |
| 7,837,691 | B2 | 11/2010 | Cordes et al. |
| 7,849,751 | B2 | 12/2010 | Clark et al. |
| 7,927,336 | B2 | 4/2011 | Rasmussen |
| 7,978,091 | B2 | 7/2011 | Boillot |
| 8,025,663 | B2 | 9/2011 | Keeven et al. |
| 8,065,927 | B2 | 11/2011 | Crottet et al. |
| 8,118,815 | B2 | 2/2012 | van der Walt |
| 8,137,361 | B2 | 3/2012 | Duggineni et al. |
| 8,141,437 | B2 | 3/2012 | Amirouche et al. |
| 8,162,951 | B2 | 4/2012 | Kaufman |
| 8,197,489 | B2 | 6/2012 | Chessar et al. |
| 8,197,549 | B2 | 6/2012 | Amirouche et al. |
| 8,211,041 | B2 | 7/2012 | Fisher et al. |
| 8,231,631 | B2 | 7/2012 | Lavallee et al. |
| 8,234,929 | B2 | 8/2012 | Clark et al. |
| 8,273,131 | B2 | 9/2012 | Metzger et al. |
| 8,303,597 | B2 | 11/2012 | Rasmussen |
| 8,323,290 | B2 | 12/2012 | Metzger et al. |
| 8,337,508 | B2 | 12/2012 | Lavallee et al. |
| 8,394,104 | B2 | 3/2013 | DiSilvestro |
| 8,414,653 | B2 | 4/2013 | Burstein et al. |
| 8,421,642 | B1 | 4/2013 | McIntosh et al. |
| 8,491,589 | B2 | 7/2013 | Fisher et al. |
| 8,506,571 | B2 | 8/2013 | Chana et al. |
| 8,551,023 | B2 | 10/2013 | Sherman et al. |
| 8,556,830 | B2 | 10/2013 | Sherman et al. |
| 8,562,617 | B2 | 10/2013 | Chessar et al. |
| 8,597,210 | B2 | 12/2013 | Sherman et al. |
| 8,603,101 | B2 | 12/2013 | Claypool et al. |
| 8,715,290 | B2 | 5/2014 | Fisher et al. |
| 8,721,568 | B2 | 5/2014 | Rock et al. |
| 8,734,454 | B2 | 5/2014 | DiSilvestro |
| 8,740,817 | B2 | 6/2014 | Sherman et al. |
| 8,758,355 | B2 | 6/2014 | Fisher et al. |
| 8,784,339 | B2 | 7/2014 | Stein et al. |
| 8,784,490 | B2 | 7/2014 | Wasielewski |
| 8,820,173 | B2 | 9/2014 | Clark et al. |
| 8,876,831 | B2 | 11/2014 | Rasmussen |
| 8,906,027 | B2 | 12/2014 | Roche |
| 8,945,026 | B2 | 2/2015 | Moser et al. |
| 8,945,132 | B2 | 2/2015 | PlaBy et al. |
| 8,945,133 | B2 | 2/2015 | Stein et al. |
| 8,974,459 | B1 | 3/2015 | Axelson, Jr. et al. |
| 8,998,910 | B2 | 4/2015 | Borja et al. |
| 8,998,917 | B2 | 4/2015 | Colquhoun et al. |
| 9,011,459 | B2 | 4/2015 | Claypool et al. |
| 9,044,218 | B2 | 6/2015 | Young |
| 9,050,107 | B2 | 6/2015 | Sordelet et al. |
| 9,050,197 | B2 | 6/2015 | Lorio et al. |
| 9,084,612 | B2 | 7/2015 | Sordelet et al. |
| 9,113,957 | B2 | 8/2015 | Axelson, Jr. et al. |
| 9,138,238 | B2 | 9/2015 | Sordelet et al. |
| 9,138,332 | B2 | 9/2015 | Harris et al. |
| 9,144,495 | B2 | 9/2015 | Lin et al. |
| 9,149,206 | B2 | 10/2015 | Claypool et al. |
| 9,168,032 | B2 | 10/2015 | Hutchison et al. |
| 9,192,391 | B2 | 11/2015 | Haines |
| 9,192,392 | B2 | 11/2015 | van der Walt et al. |
| 9,216,097 | B2 | 12/2015 | Hauri et al. |
| 9,241,801 | B1 | 1/2016 | Parry et al. |
| 9,248,030 | B2 | 2/2016 | Amirouche |
| 9,265,462 | B2 | 2/2016 | McIntosh et al. |
| 9,271,756 | B2 | 3/2016 | van der Walt et al. |
| 9,307,929 | B2 | 4/2016 | Colwell, Jr. et al. |
| 9,339,226 | B2 | 5/2016 | van der Walt et al. |
| 9,351,850 | B2 | 5/2016 | Fischer et al. |
| 9,370,375 | B2 | 6/2016 | Kaneyama et al. |
| 9,381,011 | B2 | 7/2016 | Ruhling et al. |
| 9,427,336 | B2 | 8/2016 | Axelson, Jr. et al. |
| 9,427,337 | B2 | 8/2016 | Claypool et al. |
| 9,439,656 | B2 | 9/2016 | Chana et al. |
| 9,456,769 | B2 | 10/2016 | Stein et al. |
| 9,480,482 | B2 | 11/2016 | Sordelet et al. |
| 9,492,179 | B2 | 11/2016 | Rasmussen |
| 9,492,180 | B2 | 11/2016 | Rasmussen |
| 9,492,186 | B2 | 11/2016 | Ghijselings |
| 9,492,290 | B2 | 11/2016 | Claypool et al. |
| 9,498,199 | B2 | 11/2016 | Colquhoun et al. |
| 9,498,235 | B2 | 11/2016 | Ghijselings |
| 9,538,953 | B2 | 1/2017 | Sherman et al. |
| 9,539,116 | B2 | 1/2017 | Claypool et al. |
| 9,545,459 | B2 | 1/2017 | Scott et al. |
| 9,554,745 | B2 | 1/2017 | Nguyen et al. |
| 9,572,586 | B2 | 2/2017 | van der Walt et al. |
| 9,572,588 | B2 | 2/2017 | Fisher et al. |
| 9,573,322 | B2 | 2/2017 | Wasielewski |
| 9,592,133 | B2 | 3/2017 | Toler et al. |
| 9,597,090 | B2 | 3/2017 | Claypool et al. |
| 9,597,096 | B2 | 3/2017 | Aghazadeh |
| 9,597,158 | B2 | 3/2017 | Colwell, Jr. et al. |
| 9,615,887 | B2 | 4/2017 | Stein et al. |
| 9,622,761 | B2 | 4/2017 | Chana et al. |
| 9,642,571 | B2 | 5/2017 | McIntosh et al. |
| 9,642,676 | B2 | 5/2017 | Stein et al. |
| 9,649,119 | B2 | 5/2017 | Rock et al. |
| 9,693,881 | B2 | 7/2017 | Lorio et al. |
| 9,724,110 | B2 | 8/2017 | Cole |
| 9,750,619 | B2 | 9/2017 | Rock |
| 9,763,807 | B2 | 9/2017 | Claypool et al. |
| 9,775,595 | B2 | 10/2017 | Vogt |
| 9,775,725 | B2 | 10/2017 | van der Walt et al. |
| 9,782,249 | B2 | 10/2017 | Hauri et al. |
| 9,808,356 | B2 | 11/2017 | Haight et al. |
| 9,820,678 | B2 | 11/2017 | Stein et al. |
| 9,839,533 | B2 | 12/2017 | Nguyen et al. |
| 9,855,057 | B2 | 1/2018 | Axelson, Jr. et al. |
| 9,901,331 | B2 | 2/2018 | Toler et al. |
| 9,962,172 | B2 | 5/2018 | Hutchison et al. |
| 9,980,735 | B2 | 5/2018 | Chana et al. |
| 9,993,354 | B2 | 6/2018 | Fisher et al. |
| 10,010,329 | B2 | 7/2018 | Sordelet et al. |
| 10,010,330 | B2 | 7/2018 | Claypool et al. |
| 10,064,671 | B2 | 9/2018 | Sharkey et al. |
| 10,070,973 | B2 | 9/2018 | Sherman et al. |
| 10,076,344 | B2 | 9/2018 | Toler |
| 10,080,617 | B2 | 9/2018 | Haider et al. |
| 10,092,362 | B2 | 10/2018 | Wasielewski |
| 10,772,640 | B2 | 9/2020 | Trabish et al. |
| 10,772,641 | B2 | 9/2020 | Trabish et al. |
| 2003/0069644 | A1 | 4/2003 | Kovacevic et al. |
| 2003/0187452 | A1 | 10/2003 | Smith et al. |
| 2004/0097951 | A1 | 5/2004 | Steffensmeier |
| 2004/0122441 | A1 | 6/2004 | Muratsu |
| 2005/0010299 | A1 | 1/2005 | Disilvestro |
| 2005/0010301 | A1 | 1/2005 | Disilvestro et al. |
| 2005/0038442 | A1 | 2/2005 | Freeman |
| 2005/0149037 | A1 | 7/2005 | Steffensmeier et al. |
| 2005/0256527 | A1 | 11/2005 | Delfosse et al. |
| 2006/0111726 | A1 | 5/2006 | Felt et al. |
| 2006/0241569 | A1 | 10/2006 | DiSilvestro |
| 2006/0241640 | A1 | 10/2006 | Briard et al. |
| 2006/0247646 | A1 | 11/2006 | Bihary |

(56) References Cited

U.S. PATENT DOCUMENTS

2007/0005073 A1 1/2007 Claypool et al.
2007/0066917 A1 3/2007 Hodorek et al.
2007/0162036 A1 7/2007 Schifrine et al.
2007/0233267 A1 10/2007 Amirouche et al.
2007/0239157 A1 10/2007 Guillaume
2007/0244488 A1 10/2007 Metzger et al.
2007/0293868 A1 12/2007 Delfosse et al.
2008/0051798 A1 2/2008 Colquhoun et al.
2008/0269596 A1 10/2008 Revie et al.
2009/0018544 A1 1/2009 Heavener
2009/0222089 A1 9/2009 Hauri et al.
2009/0264894 A1 10/2009 Wasielewski
2009/0270869 A1 10/2009 Colquhoun et al.
2010/0191068 A1 7/2010 Bewernitz et al.
2010/0198275 A1 8/2010 Chana et al.
2010/0249533 A1 9/2010 Pierce et al.
2010/0249534 A1 9/2010 Pierce et al.
2010/0249535 A1 9/2010 Pierce et al.
2010/0249665 A1 9/2010 Roche
2010/0249787 A1 9/2010 Roche
2010/0249788 A1 9/2010 Roche
2010/0249790 A1 9/2010 Roche
2010/0249791 A1 9/2010 Roche
2010/0250276 A1 9/2010 Pierce et al.
2010/0250284 A1 9/2010 Roche et al.
2010/0250571 A1 9/2010 Pierce et al.
2011/0046685 A1 2/2011 Faure et al.
2011/0196370 A1 8/2011 Mikhail
2011/0213221 A1 9/2011 Roche
2012/0172762 A1 7/2012 Boyer et al.
2012/0172881 A1 7/2012 Hutchison
2012/0179069 A1 7/2012 Amirouche
2012/0259342 A1 10/2012 Chana et al.
2012/0290088 A1 11/2012 Amirouche et al.
2013/0023794 A1 1/2013 Stein et al.
2013/0023795 A1 1/2013 Stein et al.
2013/0030538 A1 1/2013 Metzger et al.
2013/0079668 A1 3/2013 Stein et al.
2013/0079669 A1 3/2013 Stein et al.
2013/0079670 A1 3/2013 Stein et al.
2013/0102929 A1 4/2013 Haight et al.
2013/0138112 A1 5/2013 Young
2013/0204157 A1 8/2013 Clark et al.
2013/0261503 A1 10/2013 Sherman et al.
2013/0261505 A1 10/2013 Sherman et al.
2013/0261631 A1 10/2013 Ruhling
2013/0261758 A1 10/2013 Claypool et al.
2013/0261759 A1 10/2013 Claypool et al.
2014/0025081 A1 1/2014 Lorio
2014/0066934 A1 3/2014 Deirmengian et al.
2014/0094715 A1 4/2014 Stein et al.
2014/0114319 A1 4/2014 Wilkinson
2014/0276861 A1 9/2014 Stein et al.
2014/0276886 A1 9/2014 Stein et al.
2014/0277214 A1* 9/2014 Helenbolt .......... A61B 17/8852
606/86 R
2014/0288563 A1 9/2014 Claypool et al.
2014/0309560 A1 10/2014 Bonutti
2015/0025537 A1 1/2015 Ghijselings
2015/0051455 A1 2/2015 Wasielewski et al.
2015/0088140 A1 3/2015 Toler et al.
2015/0105782 A1 4/2015 D'Lima et al.
2015/0201886 A1 7/2015 Clark et al.
2015/0209158 A1 7/2015 Reeve
2015/0230804 A1 8/2015 Chana et al.
2015/0238202 A1 8/2015 Collins et al.
2015/0265291 A1 9/2015 Wilkinson
2015/0359642 A1 12/2015 Claypool et al.
2016/0007909 A1 1/2016 Singh et al.
2016/0106409 A1 4/2016 Moholkar
2016/0135825 A1 5/2016 Toler
2016/0175117 A1 6/2016 Colwell, Jr. et al.
2016/0228193 A1 8/2016 Moctezuma de la Barrera et al.
2016/0278754 A1 9/2016 Todorov et al.
2016/0278787 A1 9/2016 Axelson, Jr. et al.
2016/0278944 A1 9/2016 D'Lima et al.
2016/0310122 A1 10/2016 Ruhling et al.
2016/0346044 A1 12/2016 Brown et al.
2017/0007225 A1 1/2017 Ferro et al.
2017/0007408 A1 1/2017 Fitz et al.
2017/0042554 A1 2/2017 Chana et al.
2017/0042558 A1 2/2017 Ghijselings
2017/0079670 A1 3/2017 Haines
2017/0079801 A1 3/2017 Drury et al.
2017/0128057 A1 5/2017 Rasmussen
2017/0128078 A1 5/2017 Rasmussen
2017/0143324 A1 5/2017 Toler et al.
2017/0156736 A1 6/2017 Claypool et al.
2017/0196515 A1 7/2017 Clark et al.
2017/0245872 A1 8/2017 Rock et al.
2017/0252186 A1 9/2017 Lorio et al.
2017/0312099 A1 11/2017 Paszicsnyek
2017/0325868 A1 11/2017 Dungy
2017/0333018 A1 11/2017 Sehat
2017/0333058 A1 11/2017 Cabot
2017/0333059 A1 11/2017 Cole
2017/0333220 A1 11/2017 Reeve
2017/0360512 A1 12/2017 Couture et al.
2017/0360576 A1 12/2017 Rock
2018/0000612 A1 1/2018 Claypool et al.
2018/0021151 A1 1/2018 Mantovani et al.
2018/0036015 A1 2/2018 Bonutti
2018/0049895 A1 2/2018 Haight et al.
2018/0085134 A1 3/2018 Uthgenannt
2018/0098774 A1 4/2018 Bonutti
2018/0132949 A1 5/2018 Merette et al.
2018/0168826 A1 6/2018 van der Walt et al.
2018/0177509 A1 6/2018 Trabish et al.
2018/0177607 A1 6/2018 Trabish et al.
2018/0177611 A1 6/2018 Trabish et al.
2018/0177612 A1 6/2018 Trabish et al.
2018/0199952 A1 7/2018 Cole
2018/0214283 A1 8/2018 Johannaber et al.
2018/0221008 A1 8/2018 Todorov et al.
2019/0008500 A1 1/2019 Plaskos et al.
2019/0110905 A1 4/2019 Cabot
2019/0167447 A1 6/2019 Angibaud
2019/0231252 A1 8/2019 Paszicsnyek
2019/0290253 A1 9/2019 Trabish et al.
2020/0155135 A1 5/2020 Cole et al.
2020/0305942 A1 10/2020 Oden et al.
2021/0259713 A1 8/2021 Trabish et al.

* cited by examiner

LOAD SENSOR BALANCER INSTRUMENTS

CROSS-REFERENCE TO RELATED APPLICATIONS

This application is a continuation of U.S. application Ser. No. 17/941,416, filed on Sep. 9, 2022, which is a divisional of U.S. application Ser. No. 16/775,430, filed on Jan. 29, 2020, the disclosures of which are hereby incorporated by reference herein in their entirety.

FIELD OF INVENTION

The present disclosure relates to an apparatus and a method for performing orthopedic procedures, and in particular to an apparatus and a method for performing joint replacement procedures.

BACKGROUND OF THE INVENTION

Joint replacement procedures generally include replacing a subject's joint with prosthetic joint components. For example, a total knee arthroplasty ("TKA") procedure includes replacement of the distal end of the femur and the proximal end of the tibia with a femoral prosthesis and a tibial prosthesis, respectively. Multiple bone resections on the distal femur and the proximal tibia are required prior to the implantations of these prostheses. Proper soft-tissue tension, joint alignment and balance are necessary for smooth and well-aligned joint movement.

Various surgical tools such as tensors, balancer, spacers, alignment guides, load indicators, etc. are generally used to perform a TKA. After the initial bone resections of the tibia and/or the femur, a surgeon determines the knee extension and flexion gaps using tools such as spacers, a tensor, or a balancer. Spacers typically consist of a set of one-piece blocks of varying thicknesses that can be inserted into the resected joint space to confirm the flexion and extension gaps. A tensor or balancer generally have multiple components including a set of paddles with telescoping means to allow for insertion into the joint space and distraction in situ. The tensor must be structurally strong enough to withstand substantial loading during flexion and extension of the knee. However, a tensor with large paddles cannot be easily located within the tight joint space, especially during the initial insertion prior to distracting the knee joint.

Knee joint balancing with the tensioner may be performed during the TKA without everting the patella. This generally requires a tensor with sufficiently long linking members and femoral/tibial paddles that are offset to the linking members for the placement of the tensioner in anterior-to-posterior direction without requiring the dislocation of the patella from the trochlear groove of the femur. However, long linking members have a tendency to induce cantilever loading and offset paddles cause torsion loading which reduces the load bearing capability of the tensor. Joint balancing may also be performed by everting the patella which may allow for the use of a tensioner without the attendant problems just mentioned. However, dislocating the patella in this manner can damage the soft tissue of the extensor mechanism. Moreover, a complete and accurate assessment of the joint's balance through a flexion-extension range of motion cannot be assessed.

Furthermore, load sensors which can be used with the tensors to provide real-time ligament tension during the TKA must be placed in contact with the paddles. These sensors further increase the size of the tensor paddles and increase the difficulty of locating the paddles in a tight joint space.

Therefore, there exists a need for an apparatus and a method that allow for soft tissue balancing and proper knee alignment during a knee replacement procedure.

BRIEF SUMMARY OF THE INVENTION

In certain embodiments, the present disclosure relates generally to a tensor with a tibial paddle that can lie within a femoral paddle and methods for performing a joint balancing using the tensor. In other embodiments, the present disclosure relates generally to a tibial spacer and balancer and methods for performing a joint balancing using the tibial spacer and balancer.

In an aspect of the present disclosure, an apparatus for performing an orthopedic procedure on a knee is provided. In accordance with this aspect, the apparatus may include a femoral paddle, a tibial paddle, a load sensor and a housing. The femoral paddle may define a thickness. The femoral paddle may have a proximal side and an opposite distal side. The proximal side may include at least one proximal femoral recess. The distal side may include a distal femoral recess. The tibial paddle may include a tibial proximal side and an opposite tibial distal side. The load sensor may be disposed in the femoral recess to indicate a load on the femoral paddle. The housing may be coupled to the tibial paddle and the femoral paddle. The housing may include a distractor to vary the distance between the tibial paddle and the femoral paddle. The tibial paddle may be disposed within the distal femoral recess in a closed position such that a combined thickness of the femoral paddle, the tibial paddle and the load sensor in the closed position may be substantially the same as the thickness.

Continuing in accordance with this aspect, the femoral paddle may include a plurality of tiered recesses within the distal femoral recess. The tibial paddle may include a plurality of tiered ribs on the tibial proximal side. Each of the plurality of tiered ribs may be disposed within a corresponding tiered recess in the closed position. At least one of the tiered ribs may contact a distal surface of the corresponding tiered recess in the closed position.

Continuing in accordance with this aspect, the femoral paddle may extend along a central femoral paddle axis. The femoral paddle axis may separate the femoral paddle into a femoral medial side and a femoral lateral side. The tibial paddle may extend along a central tibial paddle axis. The tibial paddle axis may separate the tibial paddle into a tibial medial side and a tibial lateral side. The femoral paddle axis and the tibial paddle axis may be parallel to each other and lie on a first plane. A femoral paddle shaft may couple the femoral paddle to the housing and a tibial paddle shaft may couple the tibial paddle to the housing. The femoral paddle shaft may extend along a femoral paddle shaft axis and the tibial paddle shaft may extend along a tibial paddle shaft axis. The femoral paddle shaft axis and the tibial paddle shaft axis may be parallel to each other and lie on a second plane. The first plane may be offset to the second plane.

Continuing in accordance with this aspect, the distractor may include a distraction screw to move the tibial paddle and/or the femoral paddle along a distraction axis transverse to the femoral paddle shaft axis and the tibial paddle shaft axis. The tibial paddle may include an aperture for receiving an anti-rotation shaft extending from the housing to prevent rotation of tibial paddle about the tibial paddle shaft axis. The housing may include an adjuster to translate the femoral paddle along an adjuster axis transverse to the distraction axis. The femoral paddle shaft may be rotatable about the femoral paddle shaft axis to rotate the femoral paddle with respect to the distraction axis. A medial load center of a medial condyle in contact with the femoral medial side may lie on a medial load center axis. A lateral load center of a later condyle in contact with the femoral lateral side may lie on a lateral load center axis. A medial offset distance measured between the medial load center axis and the femoral paddle shaft axis along the femoral paddle may be less than a lateral offset distance measured between the lateral load center axis and the femoral paddle shaft axis along the femoral paddle. The lateral offset distance may allow the femoral paddle and tibial paddle to be placed between a femur and a tibia in posterior-anterior direction without everting a patella.

In a further aspect of the present disclosure, an apparatus for performing an orthopedic procedure on a knee is provided. An apparatus according to this aspect may include a femoral paddle, a tibial paddle and a housing. The femoral paddle may define a thickness. The femoral paddle may have a proximal side and an opposite distal side. The proximal side may include at least one proximal femoral recess. The distal side may include a distal femoral recess. The tibial paddle may include a tibial proximal side and an opposite tibial distal side. The housing may be coupled to the tibial paddle and the femoral paddle. The housing may include a distractor to vary the distance between the tibial paddle and the femoral paddle. The tibial paddle may be disposed within the distal femoral recess in a closed position. A combined thickness of the femoral paddle and the tibial paddle in the closed position may be equal to the thickness.

Continuing in accordance with this aspect, a load sensor may be disposed in the femoral recess to indicate a load on the femoral paddle.

In a further aspect of the present disclosure, a method of performing an orthopedic procedure on a knee is provided. A method according to this aspect may include the steps of resecting a proximal tibia, placing a femoral paddle and a tibial paddle of a tensor in a closed position without everting a patella, distracting the knee joint using a housing coupled to the tibial paddle and the femoral paddle, and measuring knee loads using a load sensor disposed in a femoral recess of the femoral paddle to indicate a load on the femoral paddle. The femoral paddle may contact an unresected distal femur. The tibial paddle may contact the resected proximal tibia in the closed position. The femoral paddle may define a thickness. The femoral paddle may have a proximal side and an opposite distal side. The proximal side may include the at least one proximal femoral recess. The distal side may include a distal femoral recess. The tibial paddle may include a tibial proximal side and an opposite tibial distal side. The housing may include a distractor to vary the distance between the tibial paddle and the femoral paddle. The tibial paddle may be disposed within the distal femoral recess such that a combined thickness of the femoral paddle, the tibial paddle and the load sensor in the closed position may be substantially the same as the thickness.

Continuing in accordance with this aspect, the method may further include the step of taking the knee joint through flexion and extension to measure knee gap and knee tension while the patella remains everted.

In a further aspect of the present invention, a method of performing an orthopedic procedure on a knee is provided. A method according to this aspect may include the steps of placing a femoral paddle and a tibial paddle of a knee balancer in a closed position, distracting the knee joint using a housing coupled to the tibial paddle and the femoral paddle, and measuring knee loads using a load sensor disposed in a femoral recess to indicate a load on the femoral paddle. The femoral paddle may contacts a distal femur and the tibial paddle may contacts a proximal tibia in the closed position. The femoral paddle may define a thickness. The femoral paddle may have a proximal side and an opposite distal side. The proximal side may include the at least one proximal femoral recess. The distal side may include a distal femoral recess. The tibial paddle may include a tibial proximal side and an opposite tibial distal side. The housing may including a distractor to vary the distance between the tibial paddle and the femoral paddle. The tibial paddle may be disposed within the distal femoral recess such that a combined thickness of the femoral paddle, the tibial paddle and the load sensor in the closed position may be substantially the same as the thickness.

In a further aspect of the present invention, a method of trialing a knee joint for determining an appropriate size for a tibial insert is provided. A method according to this aspect may include the steps of inserting first and second members into a space between a tibia and a femur, engaging a first concave surface of the first member with a first condylar portion of a femoral component or femur, operating an adjustment mechanism to move the first and second members apart a first known distance corresponding to a first size tibial insert, and articulating the first condylar portion of the femoral component or femur with the first condylar portion of a tibial component or tibia through a range of flexion and extension motion to assess the knee joint at the first known distance. The first and second members may be connected to an adjustment mechanism. The first member may have the first condylar portion defining a first concave surface.

Continuing in accordance with this aspect, the second member may include a first plate and a first arm. The first plate may include the first condylar portion of the first member. The first arm may be connected to the adjustment mechanism. The method may further include the step of connecting the first arm to the first plate. The step of connecting the first arm to the first plate may include sliding the first arm in a lateral-medial direction into a recess defined in a bottom side of the first plate. The step of connecting the first arm to the first plate may include sliding the first arm in an anteroposterior direction into a recess defined in a bottom side of the first plate.

Continuing in accordance with this aspect, the method may include the step of operating the adjustment mechanism to move the first and second members apart a second known distance corresponding to a second size tibial insert, articulating the first condylar portions of the first member and femoral component to assess the knee joint at the second known distance.

Continuing in accordance with this aspect, the operating step may be performed by rotating a rack engaged to a pinion.

Continuing in accordance with this aspect, the engaging step may include engaging a second concave surface of a second condylar portion of the first member with a second condylar portion of a femoral component.

Continuing in accordance with this aspect, the method may further include engaging a bone contact surface of the second member with a resected proximal surface of the tibia. The second member may include a second plate and a second arm. The second plate may include the bone contact surface. The second arm may be connected to the adjustment mechanism. The method may further include connecting the second arm to the second plate.

In a further aspect of the present disclosure, a tibial trial system is provided. A tibial trial system according to this aspect may include an upper plate with an upper articular surface, an upper arm, a lower arm and an adjustment mechanism connected to the upper and lower arms. The upper articular surface may have condylar portions each defining a concave surface configured to articulate with a corresponding condylar portion of a femoral component. The adjustment mechanism may be configured to move the upper and lower arms relative to each other. The upper arm may be separately formed from the upper plate and may be connectable to the upper plate.

Continuing in accordance with this aspect, the adjustment mechanism may be connected to a respective outer end of each of the upper arm and lower arm and configured to adjust a spacing between the upper and lower arms in a proximal-distal direction when the upper and lower arms are disposed between a proximal tibia and distal femur.

Continuing in accordance with this aspect, the adjustment mechanism may be a rack and pinion mechanism. The adjustment mechanism may include a shaft extending in a transverse direction relative to a direction of the spacing and may include a series of teeth extending along the shaft. A gear may be disposed within a housing and operatively engaged with the series of teeth. The shaft may be connected to the upper arm. The housing may be connected to the lower arm.

Continuing in accordance with this aspect, the upper plate may have a lower side opposite the articular surface. The lower side may define a recess configured to receive the upper arm. The recess may extend in a lateral-medial direction such that the upper arm may be slidingly received by the recess from a lateral or medial side of the upper plate. The recess may extend in an anteroposterior direction such that the upper arm may be slidingly received by the recess from an anterior side of the upper plate. The recess may define a pair of opposing grooves which may be configured to receive opposing side edges of the upper arm.

Continuing in accordance with this aspect, the system may include a lower plate having a bone contact surface configured to engage a proximal resected surface of a tibia. The lower arm may be configured to connect to the lower plate.

Continuing in accordance with this aspect, the lower arm may have a planar bone contact surface configured to engage a proximal resected surface of a tibia.

In a further aspect of the present disclosure, an adjustable tibial trial insert assembly is provided. An adjustable tibial trial insert assembly according to this aspect may include an upper plate, an upper arm, a lower arm and an adjustment mechanism. The upper plate may include an upper articular surface configured to allow a femoral component to articulate through a range of motion in flexion and extension therewith. The upper arm may be releasably connected to the upper plate and extend in a transverse direction relative to an axis of the tibia when the upper arm is disposed between a proximal tibia and a distal femur. The lower arm may extend in the transverse direction. The adjustment mechanism may be connected to each of the upper arm and lower arm and configured to adjust a spacing between the upper plate and the lower plate.

Continuing in accordance with this aspect, the lower arm may have a planar surface configured to contact a proximal resected surface of a tibia.

Continuing in accordance with this aspect, the trial insert may further include a lower plate that may have a lower surface configured to engage a proximal resected surface of a tibia. The upper arm may be releasably connected to the lower plate.

Continuing with this aspect, the articular surface may include a pair of concave surfaces for engaging respective distal condyles of a femoral component. The concave surfaces may each extend in an anteroposterior direction. The upper arm and the lower arm may extend in a lateral-medial direction.

BRIEF DESCRIPTION OF THE DRAWINGS

A more complete appreciation of the subject matter of the present disclosure and the various advantages thereof can be realized by reference to the following detailed description, in which reference is made to the following accompanying drawings.

DETAILED DESCRIPTION

In describing preferred embodiments of the disclosure, reference will be made to directional nomenclature used in describing the human body. It is noted that this nomenclature is used only for convenience and that it is not intended to be limiting with respect to the scope of the invention.

As used herein, when referring to bones or other parts of the body, the term "anterior" means toward the front part or the face, and the term "posterior" means toward the back of the body. The term "medial" means toward the midline of the body, and the term "lateral" means away from the midline of the body. The term "superior" means closer to the heart, and the term "inferior" means more distant from the heart.

Reference will now be made in detail to the various embodiments of the present disclosure illustrated in the accompanying drawings. Wherever possible, the same or like reference numbers will be used throughout the drawings to refer to the same or like features. It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described. As used herein, the terms "distractor" and "tensor" will be used interchangeably and as such, unless otherwise stated, the explicit use of either term is inclusive of the other term. Similarly, the terms "aperture," "hole," and "recess" will be used interchangeably and as such, unless otherwise stated, the explicit use of either term is inclusive of the other term.

Figure 1:
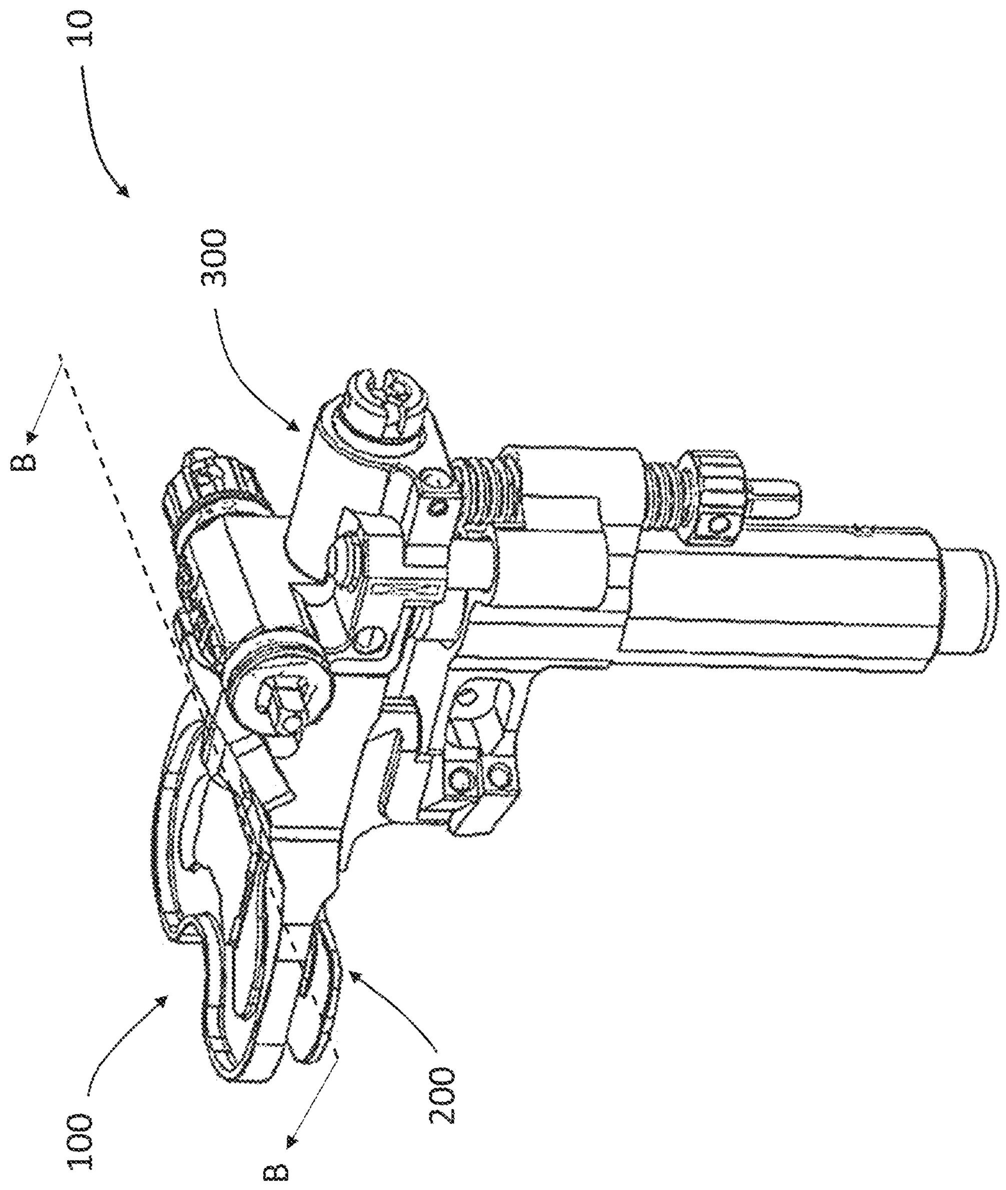
FIG. 1 is a perspective side view of a tensor of the present disclosure.

Referring now to FIG. 1, there is shown a perspective view of a tensor 10 according to an embodiment of the present disclosure. Tensor 10 includes a femoral paddle 100 and a tibial paddle 200 attached to a housing 300. Tensor 10 can be used to perform various functions during a TKA procedure to achieve the desired knee joint biomechanics as more fully described below. While tensor 10 described herein is configured to be placed in a subject's left knee joint in an anterior-to-posterior direction, it should be understood that the features of tensor 10 are similar for a tensor configured to be placed in a subject's right knee in an anterior-to-posterior direction. It is also envisioned that tensor 10 can be placed in subject's knee joint from a posterior-to-anterior, medial-to-lateral, or lateral-to-medial direction. In such embodiments, housing 300 connects to femoral and tibial paddles 100, 200 at different locations depending on the approach. For example, where the approach is lateral-to-medial, housing 300 connects to a lateral side of paddles 100, 200.

Figure 2:
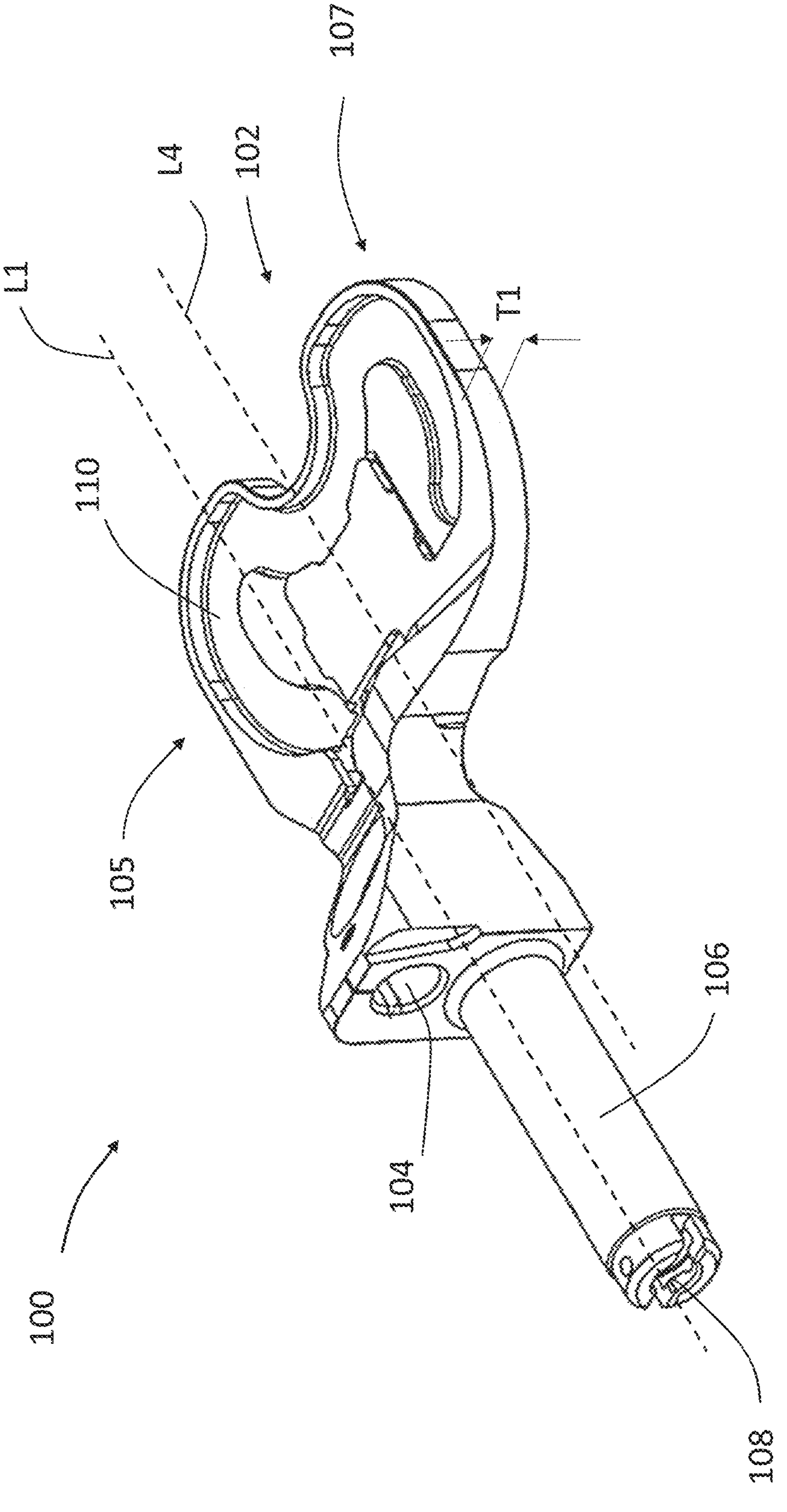
FIG. 2 is a perspective top view of a femoral paddle of the tensor of FIG. 1.

FIG. 2 shows a top view of femoral paddle 100 of tensor 10. Femoral paddle 100 includes a femoral plate 102 having a thickness T1. Femoral plate 102 extends along a femoral plate axis L4, which divides femoral plate 102 into a femoral lateral side 107 and a femoral medial side 105. A recess 110 runs along the peripheral edge of femoral plate 102 and serves as a receptacle to receive a load sensor. A shaft 106 extending from femoral plate 102 along a shaft axis L1 couples femoral paddle 100 to housing 300. Shaft 106 can be rotated either manually or with a suitable tool around shaft axis L1. A groove or notch 108 at the distal of shaft 106 allows for attachment of the tool that can be used to rotate femoral plate 102. As best shown in FIG. 2, shaft axis L1 is offset from femoral plate axis L4. Femoral paddle 100 includes a slot 104 to receive a corresponding post from housing 300 as explained below.

Figure 3:
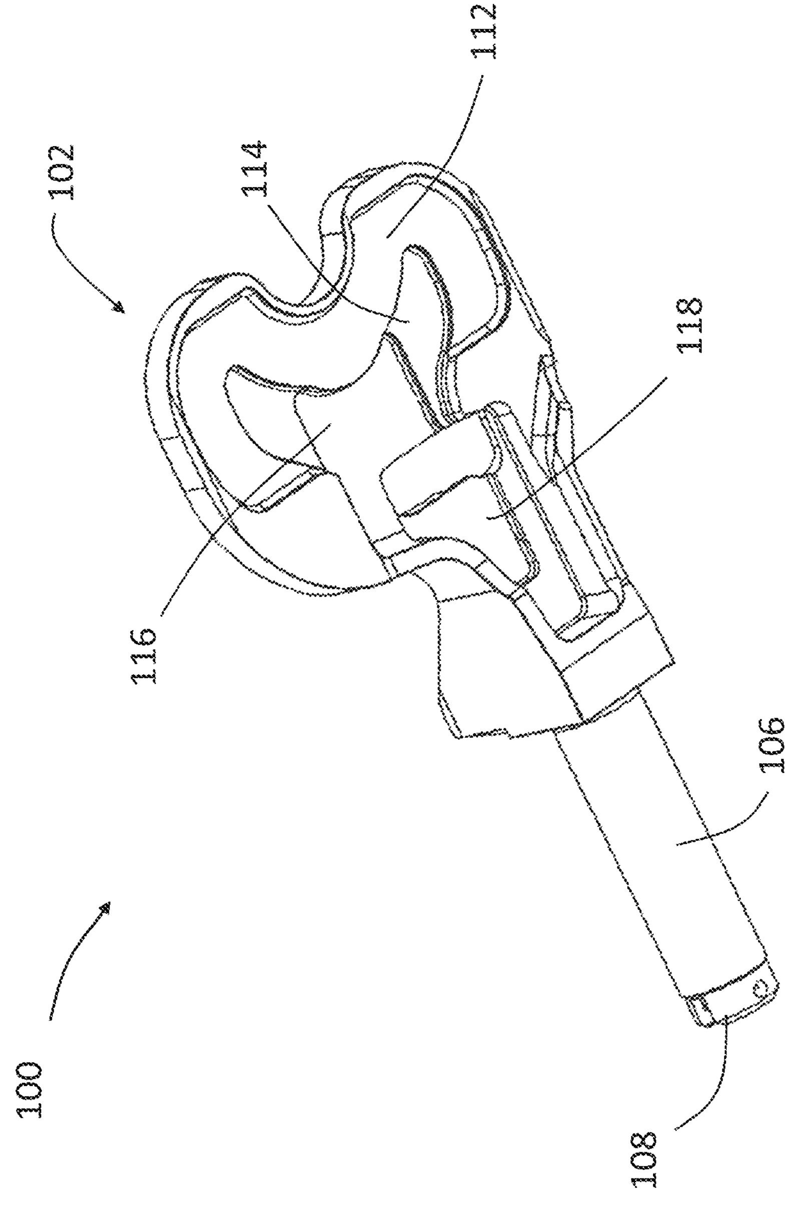
FIG. 3 is a perspective bottom view of the femoral paddle of FIG. 2.

Referring now to FIG. 3, there is shown a bottom view of femoral paddle 100. Tiered pockets 112, 114, 116, 118 are located across femoral lateral side 107 and femoral medial side 105. The tiered pockets are sized and positioned to receive corresponding tiered ribs from tibial paddle 200 as more fully described below. In addition, tiered pockets 112, 114, 116, and 118 are located at different depths within paddle 100.

Figure 4:
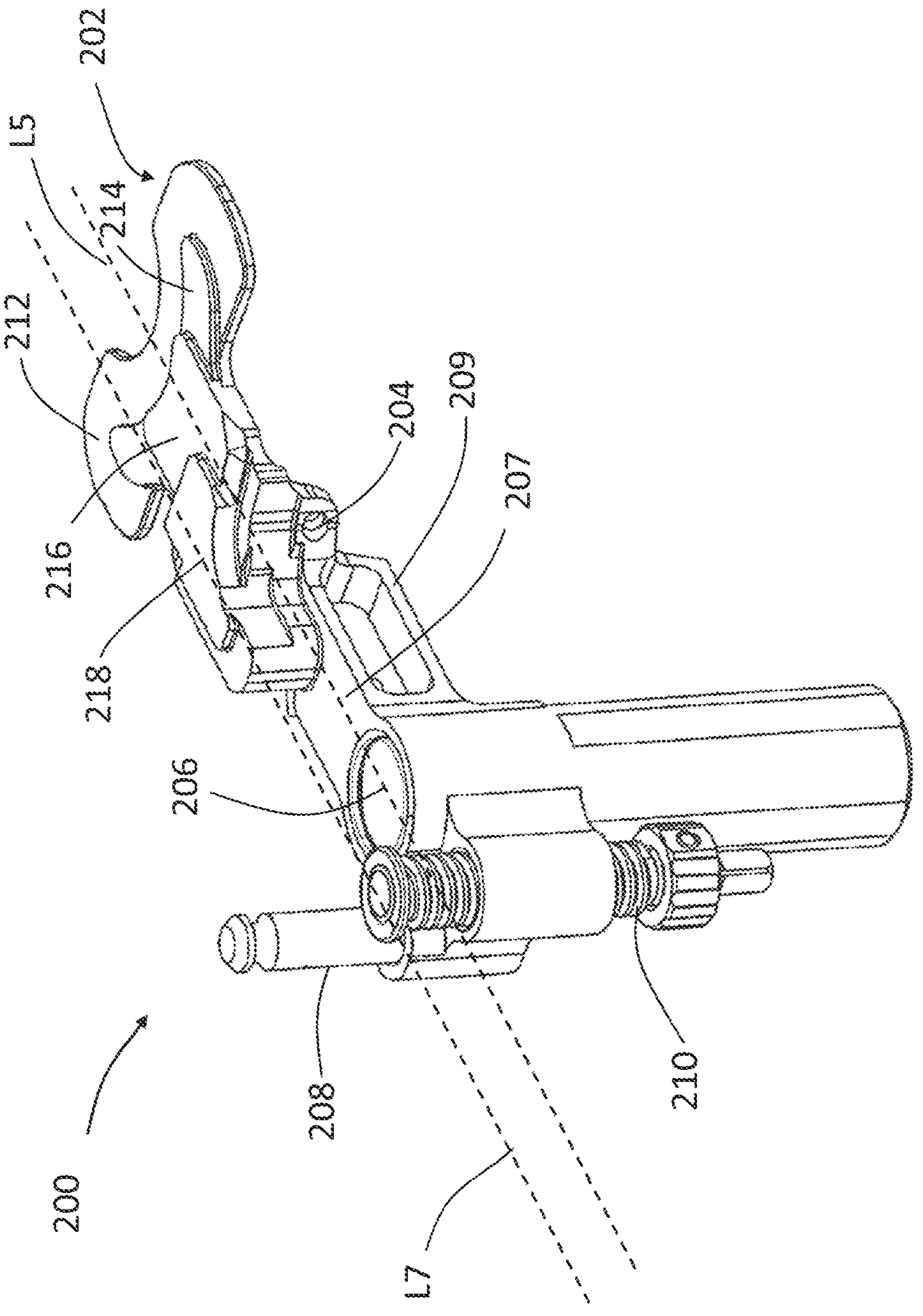
FIG. 4 is a perspective side view of a tibial paddle of the tensor of FIG. 1.

FIG. 4 shows a top view of tibial paddle 200. Tibial paddle includes a tibial plate 202 extending along a tibial plate axis L5. A tibial shaft 207 extends from tibial plate 202 along a shaft axis L7. Tibial shaft axis L7 and shaft axis L1 lie on a first plane parallel to a second plane containing the femoral plate axis L4 and the tibial plate axis L5 (not shown). The tibial shaft includes structural reinforcements such as structure 209 to structurally strengthen tensor 10 and maximize load capacity of the tensor. A bore 206 located on tibial shaft 207 extends transverse to the tibial shaft and is configured to receive a corresponding shaft from housing 200. A distraction mechanism—e.g., a screw 210 attached to bore 206 in this embodiment, allows for translation of femoral paddle 100 in reference to tibial paddle 200. An anti-rotation post 208 configured to be received in a corresponding recess of housing 300 prevents rotation of tibial paddle 300. Various holes 204 located on tibial paddle 200 serve as drill guides or alignment references during a balancing procedure. A set of tiered ribs 212, 214, 216 and 218 are provided on a proximal side of tibial plate 202 as best shown in FIG. 4. Such tiered ribs 212, 214, 216, and 218 extend from the proximal side at differing heights which correspond to the depths of the respective tiered pockets 112, 114, 116, and 118. In this regard, each tiered rib is configured to lie within a corresponding tiered pocket of femoral plate 102. When tibial plate 202 and femoral plate 102 are brought together by the distraction mechanism, the tiered ribs 212, 214, 216, 218 of tibial plate 202 are designed to be positioned within the corresponding pockets 112, 114, 116, 118 of femoral plate 102 such that tibial plate 202 lies completely within femoral plate 102.

Figure 11C:
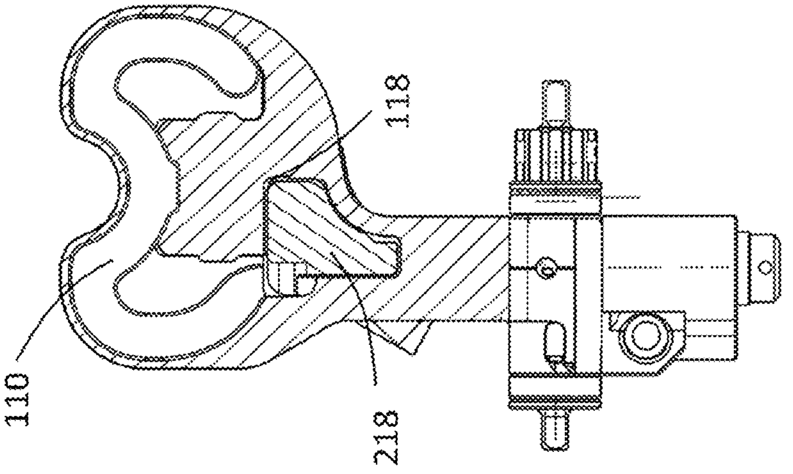
FIGS. 11A-C are top cross-sectional views of the femoral paddle and the tibial paddle of the tensor of FIG. 1.
Figure 11B:
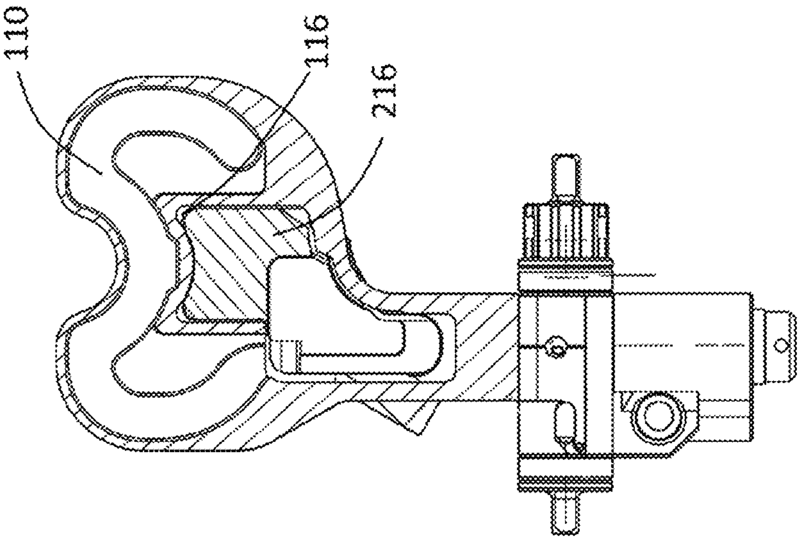
Figure 11A:
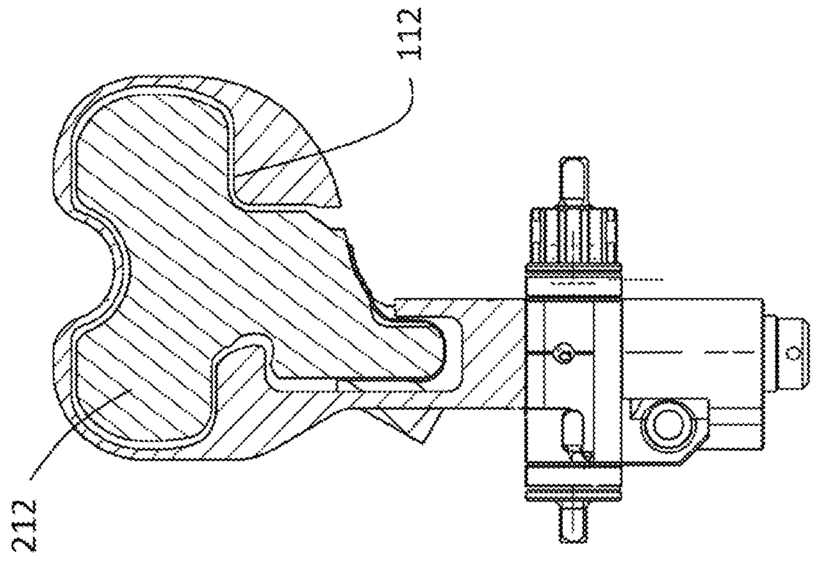

FIGS. 11A-11C show cross-sectional views of the tiered rib and pocket interface of tensor 10 in a collapsed state when the tibial plate 202 lies entirely within femoral plate 102. As shown in FIG. 11A, tiered rib 212 of tibial plate 202 is received within pocket 112 of femoral plate 102. Similarly, tiered rib 216 is received in pocket 116 (FIG. 11B) and tiered rib 218 is received in pocket 118 (FIG. 11C) when tensor 10 is in the collapsed state. The tiered rib and pocket interface allow for increased load bearing capacity of tensor 10 while simultaneously ensuring a low paddle profile to allow the tensor to be placed in the narrow gap between a femur and a tibia. For example, the combined thickness T1 of the femoral paddle, sensor array and the tibial paddle is constructed to be 6.1 mm or less. Despite this low profile, the tiered pockets, tiered ribs and reinforcing gussets enable the tensor to be robust enough to withstand at least 200 pounds per condyle or a total of at least 400 pounds. While a femoral plate with tiered pockets and a tibial plate with tiered ribs is shown in the present embodiment, in another embodiment the femoral plate can have tiered ribs and the tibial plate can have corresponding tiered recesses.

Figure 5:
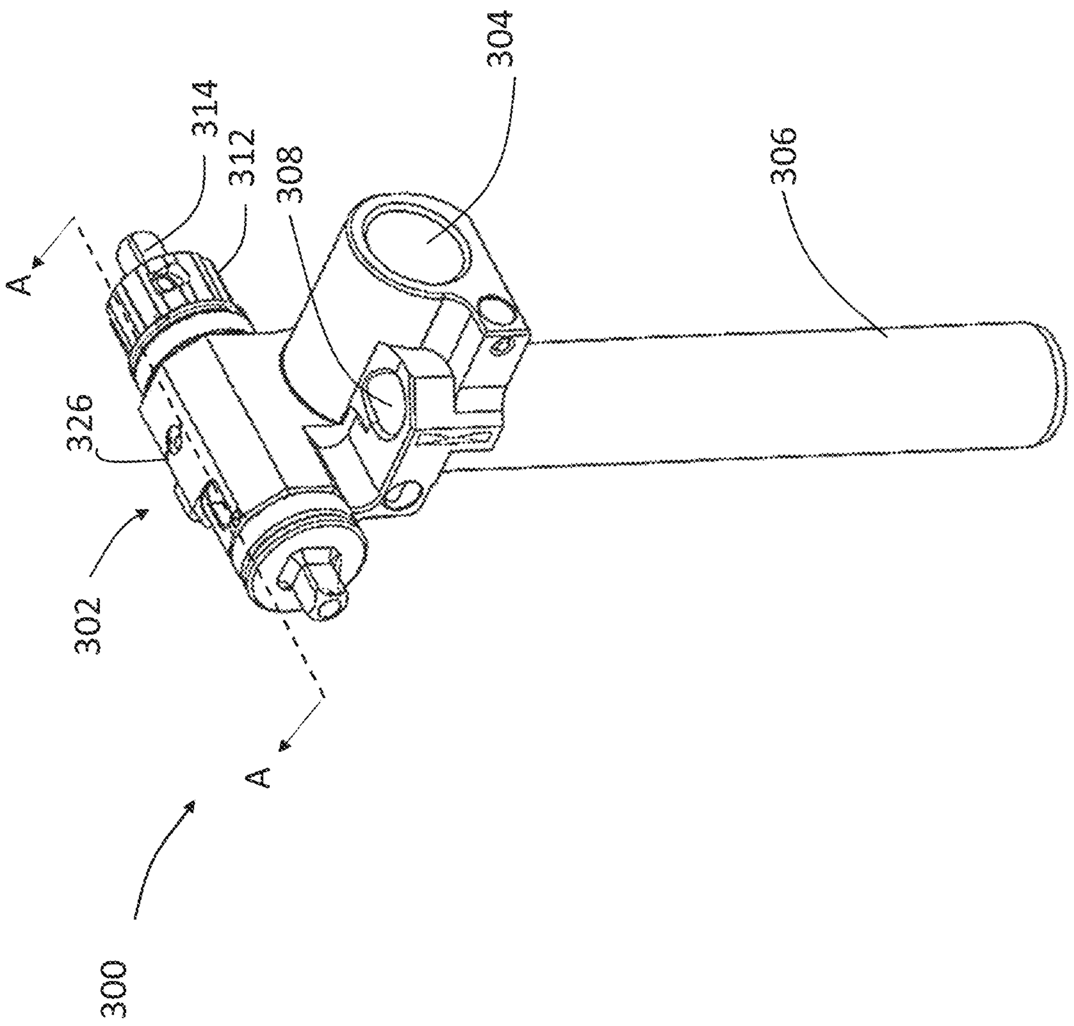
FIG. 5 is a perspective side view of a housing of the tensor of FIG. 1.

Referring now to FIG. 5, a perspective view of housing 300 is shown. Housing 300 includes a shaft 306 designed to be placed in bore 206 to couple the housing with tibial paddle 200. A bore 304 extending transverse to shaft 306 is configured to receive shaft 106 of femoral paddle 100 to couple the housing with the femoral paddle. A bore 308 is configured to receive anti-rotation post 208 from tibial paddle 200 in order to prevent rotation of tibial paddle 200 with reference to housing 300. An adjuster 302 for varying varus-valgus of the joint is located on housing 300 allowing for linear translation of femoral plate 102 as more fully explained below.

Figure 6:
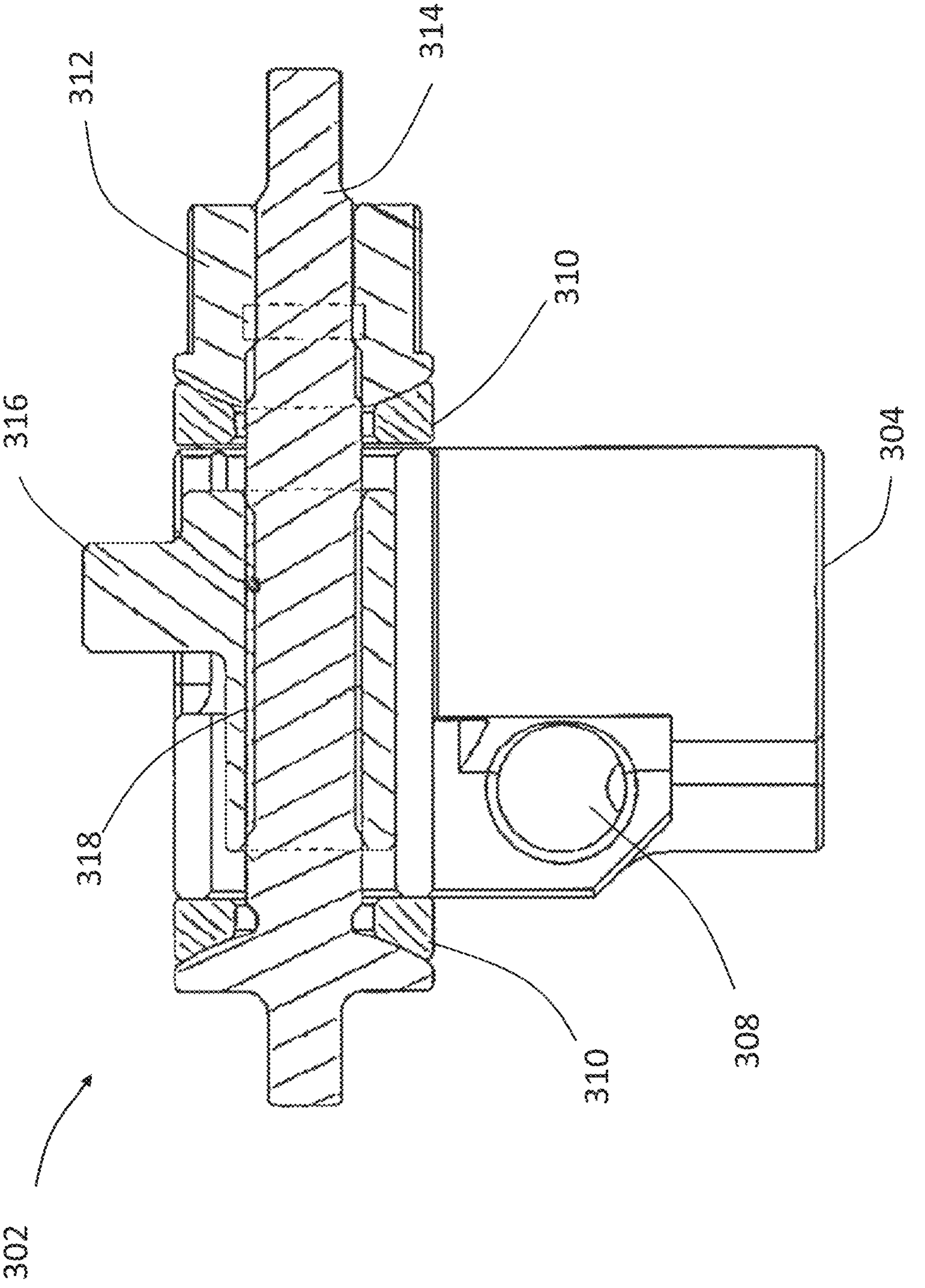
FIG. 6 is a side cross-sectional view of an adjuster along line A-A of the housing of FIG. 5.

FIG. 6 shows a cross-sectional view of adjuster 302 along line A-A of FIG. 5. Adjuster 302 includes a screw 314 located between end washers 310 and an end cap 312. The adjuster has a post 316 extending from screw 314 that can be placed in slot 104 of femoral paddle 100. Screw threading 318 of screw 314 allow the adjuster to translate the femoral plate 102 via post 316. This translation allows for varus-valgus adjustment of the knee described below. End washers 310 and end cap 312 restrict movement of the femoral paddle confining translation of the femoral plate to rotation of screw 314.

Figure 7:
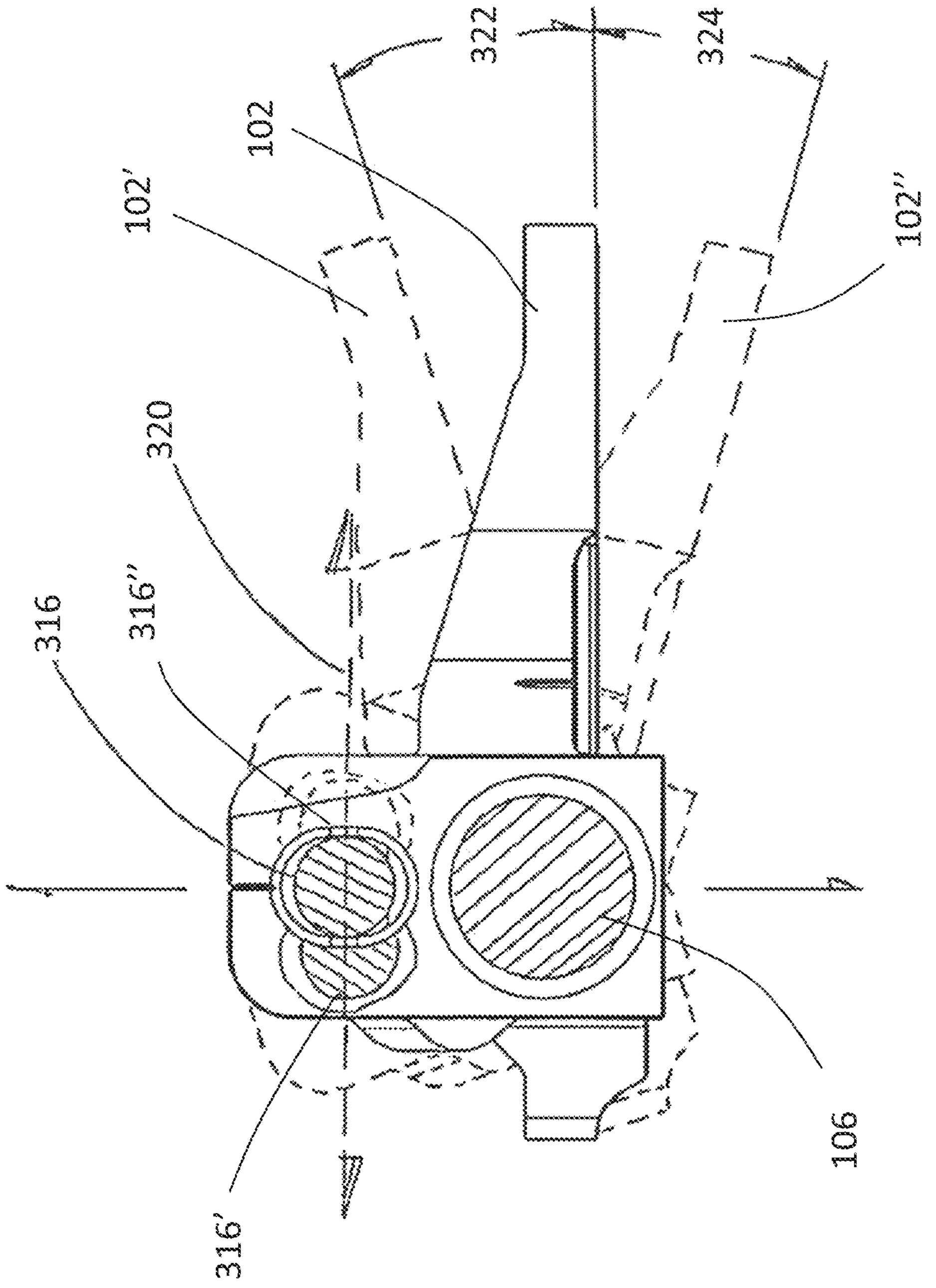
FIG. 7 is a partial side cross-sectional view of the tensor of FIG. 1 along line B-B.

FIG. 7 shows a cross-sectional view along line B-B of FIG. 1 depicting the various adjustment mechanisms of tensor 10. Shaft 106 of femoral paddle 100 can be rotated about shaft axis L1 to move femoral paddle 102 to various positions to adjust varus/valgus rotation of the knee for a desired joint orientation. For example, shaft 106 can be rotated counterclockwise to locate femoral plate to a second position 102' to provide a valgus rotation angle 322. Similarly, shaft 106 can be rotated in an opposite clockwise direction to locate femoral plate to a third position 102" to provide a varus rotation angle 324 as best shown in FIG. 7. Adjuster 302 allows for linear translation of femoral plate 102 along a translation axis 320 transverse to shaft axis L1. As indicated by the position of post 316, adjuster 302 can move the femoral plate from the first location to a second location 316' or a third location 316" in the opposite direction. The linear translation along translation axis 320 allows a surgeon to control internal and external rotation of the joint. A rotation indicator 326 on adjuster 302 indicates the external or internal rotation of femoral plate 102 as best shown in FIG. 5

Figure 8:
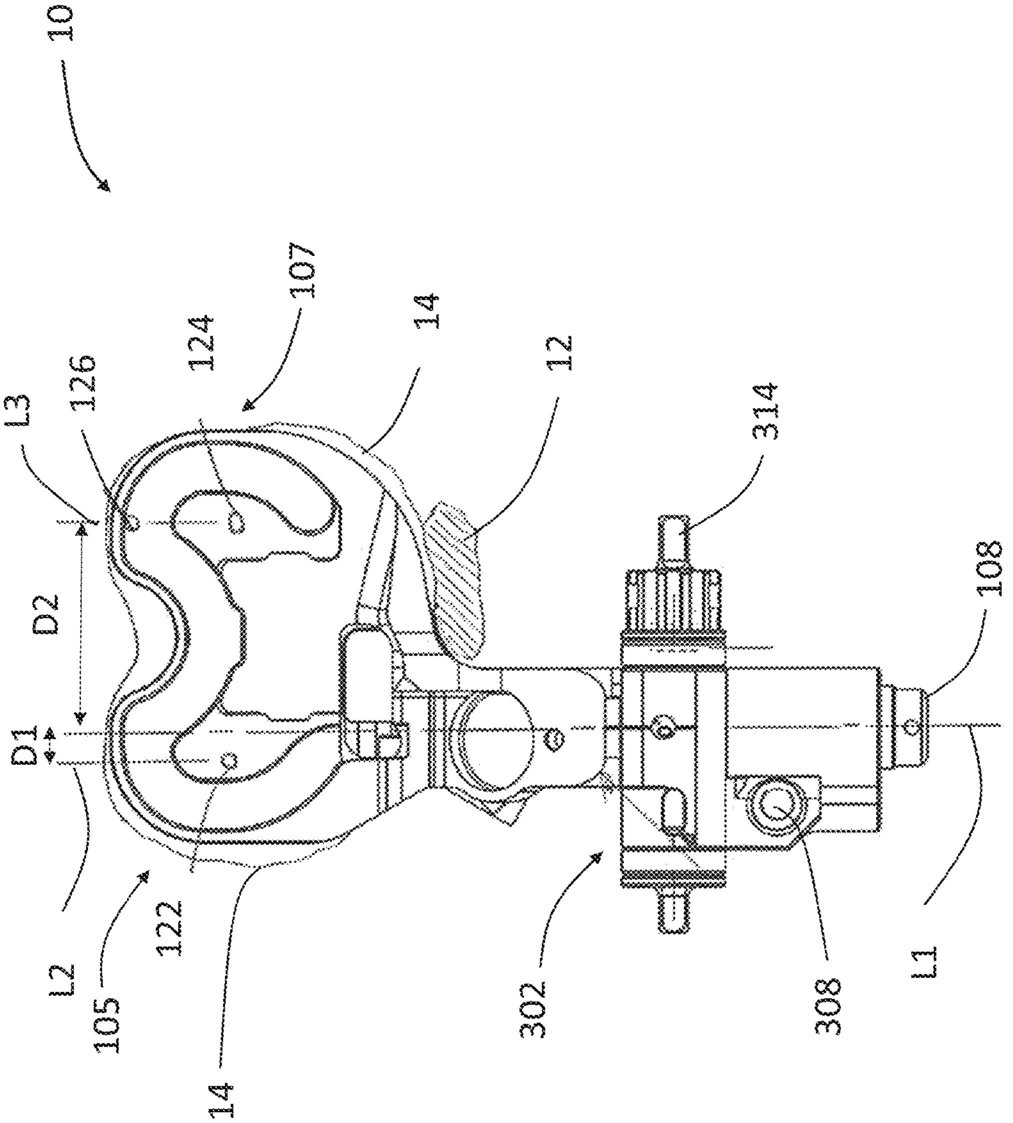
FIG. 8 is a schematic top view of the tensor of FIG. 1 placed in a knee joint.

Referring now to FIG. 8, there is shown a schematic top view of tensor 10 placed over a resected tibia 14 with patellar tendon 12 being moved laterally away to accommodate the femoral and tibial paddles of tensor 10. As shown here, the shaft lengths (femoral shaft 106 and tibial shaft 207) and the plate offsets from shaft axis L1 (femoral plate 102 and tibial plate 202), allow tensor 10 to be located in the knee joint without everting the patella. Femoral load centers during extension and flexion of the knee joint are also shown in FIG. 8. A load center 122 on femoral medial side 105 of femoral plate 102 is located on medial load axis L2 representing a femoral medial condyle load during extension and flexion of the knee joint. Load center 122 is offset from shaft axis L1 by a distance D1. Femoral lateral side 107 includes a first load center 124 representing the lateral condyle load in extension of the knee, and a second load center 126 representing the lateral condyle load in flexion. Load centers 124 and 126 lie on lateral load axis L3 as shown in FIG. 8, which is offset from shaft axis L1 by a distance D2. As distance D2 is greater than D1, tensor 10 will be subject torsional loads during balancing. However, the plate offsets allow tensor 10 to be placed in anterior-to-posterior direction in a subjects left knee joint without requiring the eversion of the subject's patella. As best shown in FIG. 8, housing 300 and shaft 106, 207 can lie medial to patellar tendon 12, while the laterally extending femoral lateral side 107 of femoral plate 102 can contact the lateral condyle of the subject. Tensor 10 can be maintained in this position while the knee is being taken through its range of motion from flexion to extension during balancing.

Figure 9:
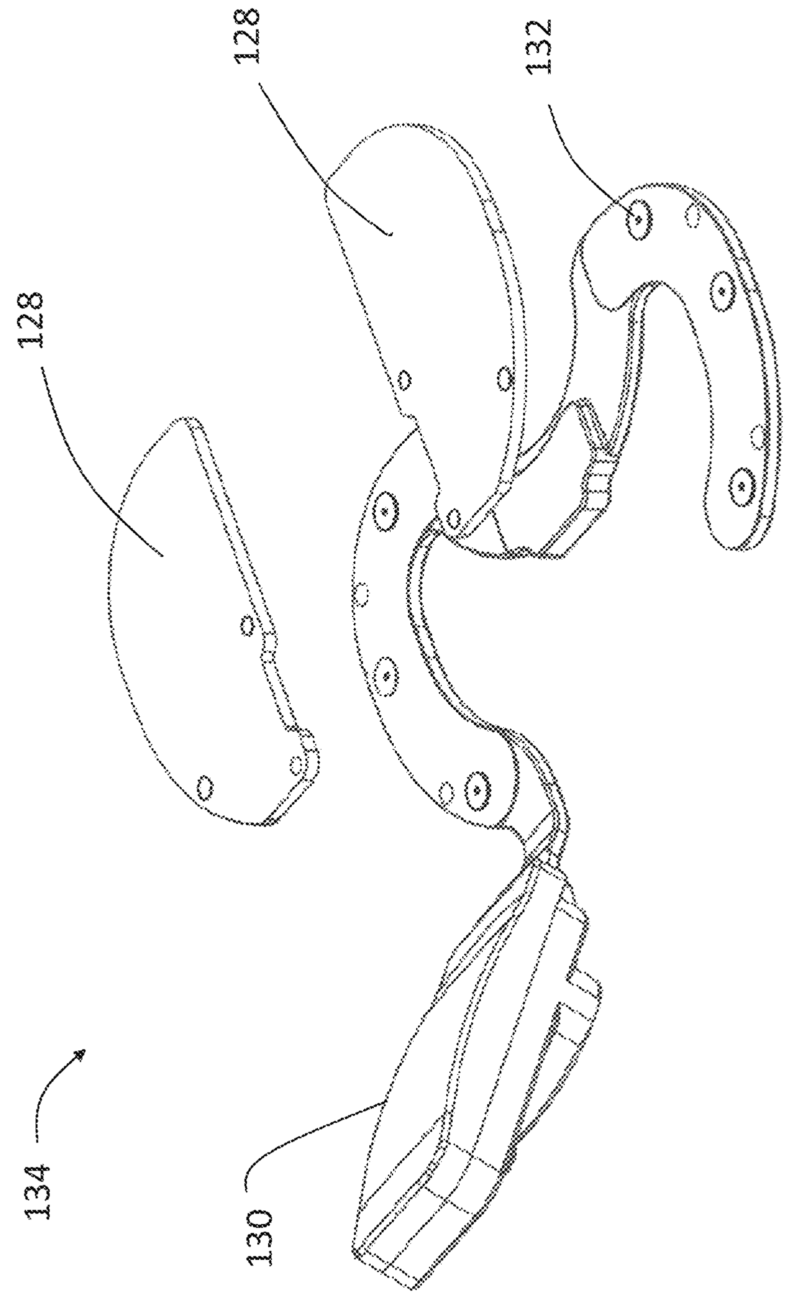
FIG. 9 is a perspective view of a load sensor of the tensor of FIG. 1.

FIG. 9 shows a perspective view of a load sensor 134 that can be placed in recess 110 of femoral plate 102. Load cells 132 and sensor load plates 134 are sized and shaped to fit within femoral plate 102 and contact load centers 122, 124 and 126 during flexion and extension to indicate femoral load values. A sensor housing 130 can include a processor, a power source and other components necessary for load reading and transmission. The sensor housing is located on the femoral shaft away from femoral plate 102 to ensure that only load cells 132 and sensor load plates 128 of load sensor 134 are located in femoral plate 102 to minimize the thickness of the femoral plate. Tensor 10 allows for convenient placement and removal of load sensor 134. While tensor 10 described herein includes a load sensor, it should be understood that tensor 10 can be used without the load sensor.

Figure 10:
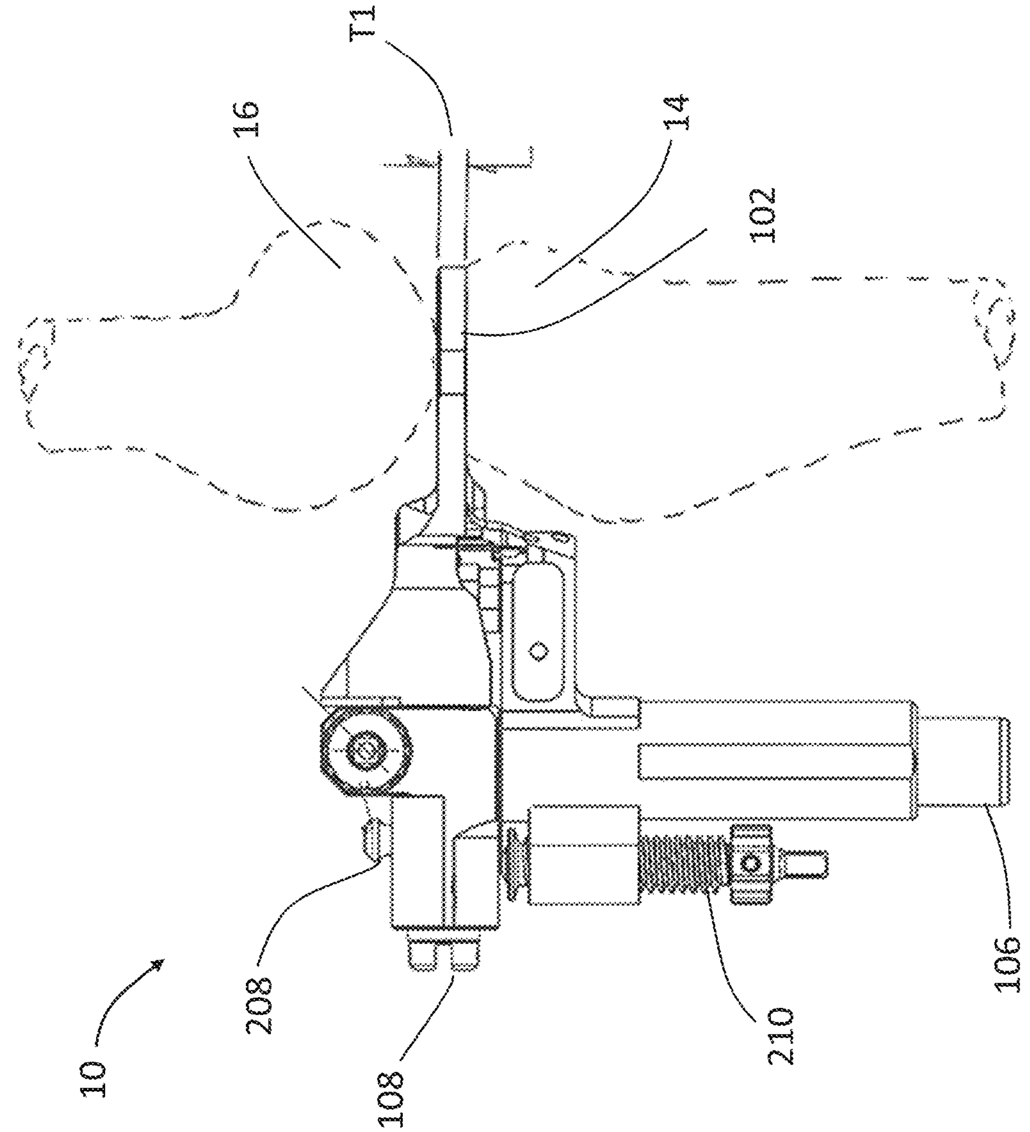
FIG. 10 is a side view of the tensor of FIG. 1 placed in a knee joint.

Referring now to FIG. 10, there is shown a side view of tensor 10 placed in a subject's knee joint. Tibial plate 202 lies entirely with femoral plate 102 when the femoral and tibial paddles are brought together as shown in FIG. 10. When the paddles are in this collapsed state, the combined thickness of the femoral plate including load sensor 134 and tibial plate is equal to thickness T1 of femoral plate. While a load sensor may lie completely within recess 110 of femoral plate 102 such that the load sensor does not extend past the thickness of femoral plate, in another embodiment the thickness of load sensor 134 may slightly extend past the femoral plate thickness.

Another aspect of the present disclosure is a method for performing a TKA with a tensor such as tensor 10. After resecting the proximal tibia 14, tensor 10 with its femoral paddle and tibial paddle fully retracted—i.e., in the collapsed state, is inserted into the knee joint as shown in FIG. 10. The low profile of tensor 10 in the collapsed state allows the tensor to be inserted in an anterior-to-posterior direction without resecting a proximal femur 16. Of course, the proximal femur can be resected prior to insertion if desired. Furthermore, as more fully described above, the shaft lengths (femoral shaft 106 and tibial shaft 207) and the plate offsets (femoral plate 102 and tibial plate 202) from shaft axis L1, allow tensor 10 to be located in the knee joint without everting the patella. Once the tensor 10 is firmly located in the knee joint, the tensor can be used to perform various functions to measure and achieve the desired knee joint biomechanics. Tensor 10 can be maintained in this position while the knee is being taken through its range of motion from flexion to extension during balancing. For example, the femoral paddle and tibial paddle can be separated using screw 210 to adjust the gap between tibia 14 and femur 16, adjuster 302 can be used to translate femoral plate 102 to adjust varus/valgus and internal/external rotation of the knee joint, and shaft 106 can be rotate to adjust varus/valgus rotation of knee joint. Furthermore, real-time load values of the lateral and medial condyles of femur 16 are measured and communicated to an operator during flexion and extension of the knee joint.

Figure 12:
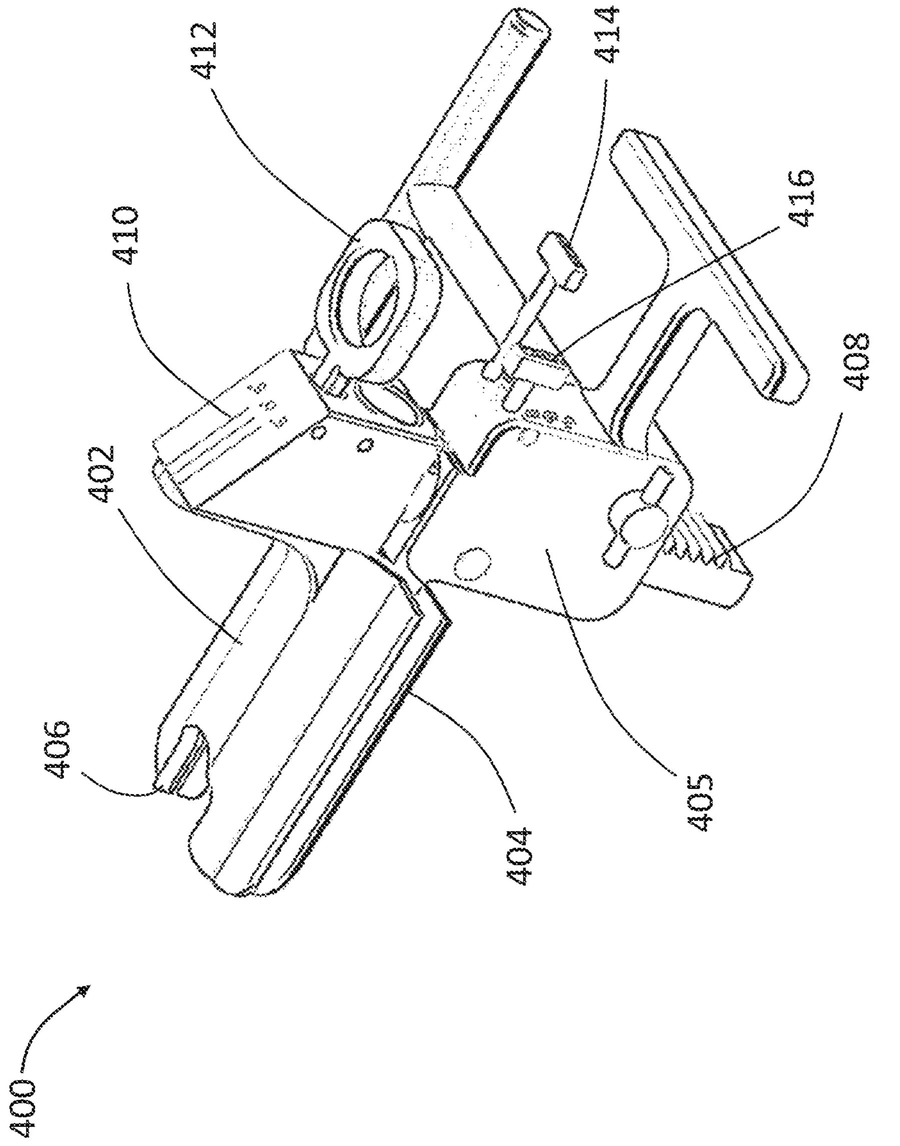
FIG. 12 is a side perspective view of a balancer according to another embodiment of the present disclosure.

Referring now to FIG. 12, there is shown a balancer 400 according to another embodiment of the present disclosure. Balancer 400 is an adjustable tibial spacer and balancer that allows for trialing of a tibial spacer during a TKA procedure. Balancer 400 includes a femoral plate 402 and a tibial plate 404 coupled to a housing 405. Housing 405 includes a rack and pinion distraction mechanism which is used to vary the distance between femoral plate 402 and tibial plate 404. A rotation indicator 410 provided on housing 405 allows for varus/valgus rotation adjustments of femoral plate 402. A lock pin 412 allows an operator to lock the varus/valgus rotation of femoral plate. The lock pin can be released to rotate the femoral plate to achieve the desired varus/valgus alignment. Once the desired varus/valgus alignment is achieved the lock pin can be activated to secure femoral plate alignment. Thickness indicators 416 indicate the tibial spacer size—i.e., distraction gap between the femoral and tibial plates, and can be locked into place once the desired tibial spacer size is achieved.

Figure 14:
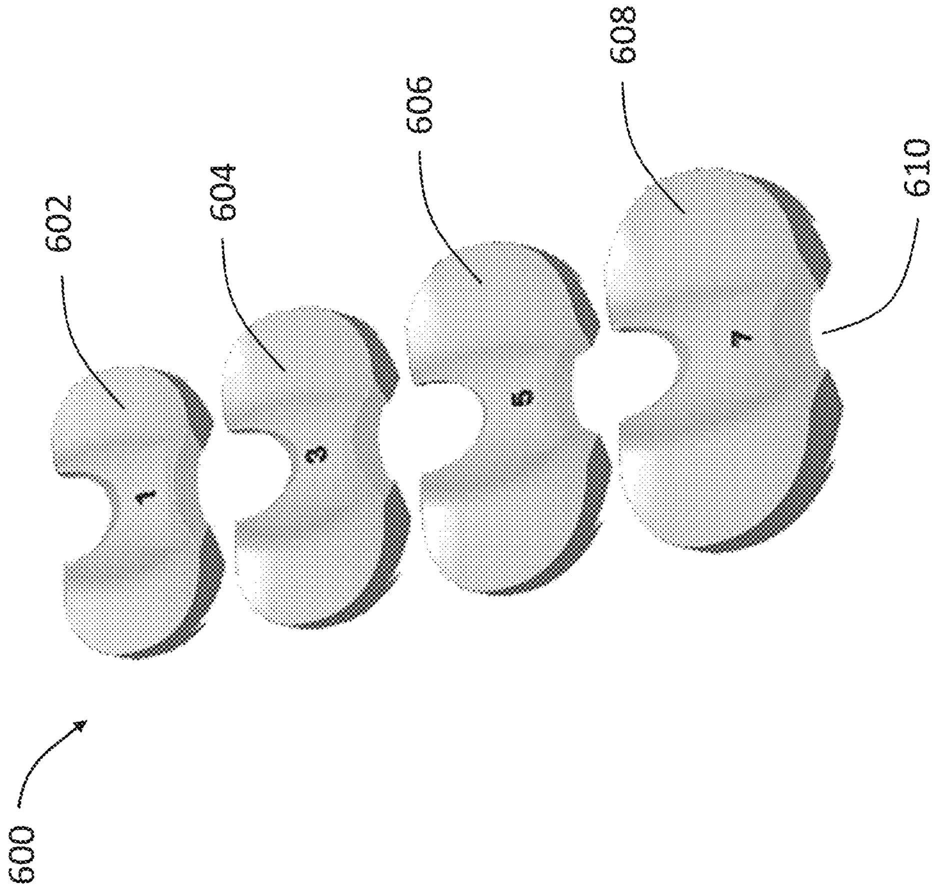
FIG. 14 is a perspective view of a set of articular tibial trials used with the balancer of FIG. 12.
Figure 13:
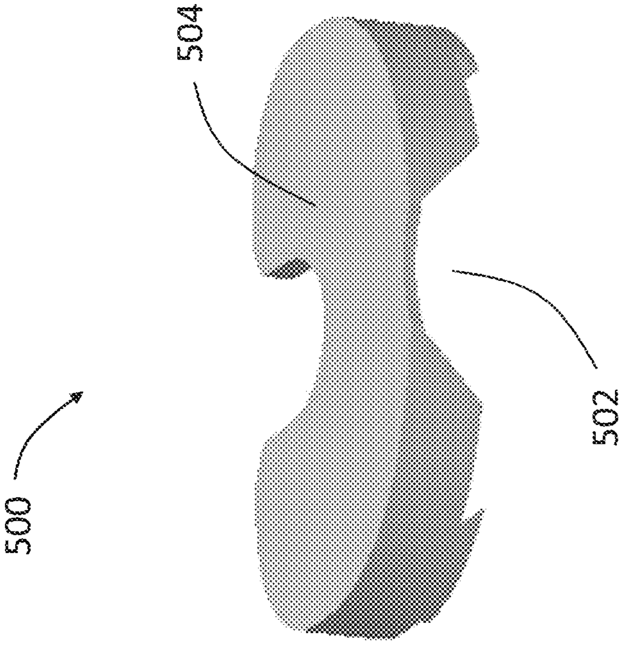
FIG. 13 is a perspective view of a flat tibial trial used with the balancer of FIG. 12.

FIGS. 13 and 14 show various attachments that can be readily attached to a distal end 406 of femoral plate 402. A flat tibial trial 500 is shown in FIG. 13. Flat tibial trial 500 includes an opening 502 shaped and sized to be removably connected to distal end of femoral plate 402. Opening 502 can have various features such as grooves, notches, tabs, etc. that can readily attached to mating features present on distal end 406 of femoral plate 402. A flat surface 504 of flat tibial trial 500 contacts a proximal femur or a femoral component when the flat tibial trial is placed in a knee joint. While opening 502 shown here extends in an anterior-to-posterior direction, another embodiment can have an opening extending in a medial-to-lateral direction. A flat tibial trial having an opening 502 extending in a medial-to-lateral direction can be slidably engaged with balancer 400 and placed in a knee joint in a medial-to-lateral direction to prevent everting of the patella during a TKA. Flat tibial trial 500 can be attached to balancer 400 and inserted to a knee joint to determine the proper tibial spacer thickness for balanced extension and flexion gaps. Thickness indicator 416 is used to lock in the desired thickness.

A set of articular tibial trials 602, 604, 606, 608 are shown in FIG. 14. The articular tibial trials are similar to flat tibial trial 500 and include an opening 610 for attachment to femoral plate 402. However, articular tibial trials include an articular surface with concave surfaces to contact medial and lateral condyles of a femur or femoral implant. The articular tibial trials allow the knee joint to be taken through a range of motion from flexion to extension by providing an articular surface for the femoral condyles to articulate during the range of motion. The articular tibial trials are provided in various sizes that can be readily attached and detached from femoral plate 402. The tibial trial sizes can be limited to a small number, as the distraction mechanism of balancer 400 can be used to adjust to trial for tibial spacers that are larger or smaller than the available tibial trials. As described above, openings 610 of articular tibial trials can extend in a medial-to-lateral direction to allow placement of the balancer 400 in a knee joint in a medial-to-lateral or lateral-to-medial direction.

Another aspect of the present disclosure is a method of trialing a tibial spacer with a balancer such as balancer 400. Flat tibial trial 500 can be readily attached to femoral plate 402 by sliding opening 502 of the flat tibial trial into distal end 406. Depending on the orientation of opening 502—i.e., anterior-to-posterior or medial-to-lateral, the balancer with the attached flat tibial trial is inserted into the knee joint in the same direction. For example, if the opening 502 extends in a lateral-to-medial direction, balancer 400 can be inserted in lateral-to-medial direction into the knee joint with the attached flat tibial trial. The femoral and tibial plates can be distracted using distraction mechanism 408 if necessary to determine the desired knee gap.

Figure 16:
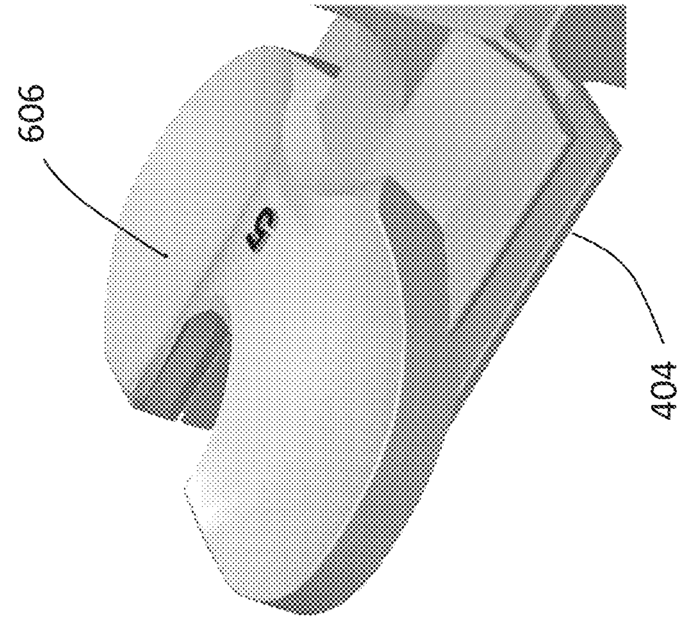
FIG. 16 is a schematic view of the articular tibial trial of FIG. 14 placed on the balancer of FIG. 12.
Figure 15:
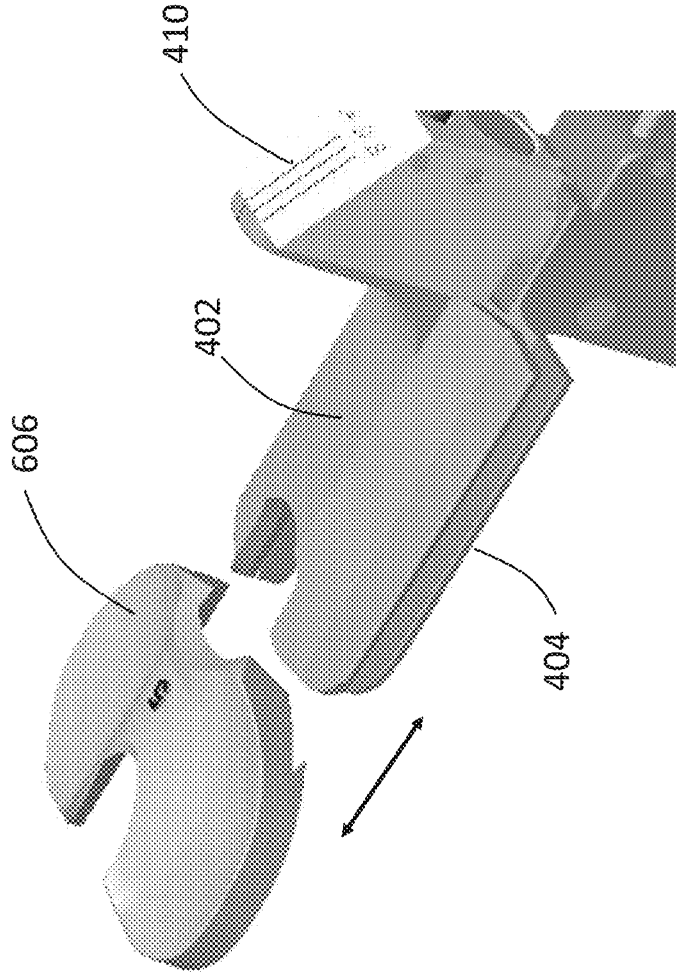
FIG. 15 is a schematic view of an articular tibial trial of FIG. 14 and the balancer of FIG. 12.

Once these desired gap is achieved, the flat tibial trial can be removed from balancer and an appropriate articular tibial trial can be attached to balancer 400. As shown in FIGS. 15, and 16 articular tibial trial 606 is slidably connected to femoral plate 402 of balancer 400. The knee joint can now be taken through a range of motion from flexion to extension to determine the desired joint biomechanics and the tibial spacer size. As attachment tibial trials can be easily attached and removed from balancer 400, balancer 400 can be removed from the attachment tibial trials once they are placed in the knee joint to facilitate convenient knee flexion and extension.

Figure 17:
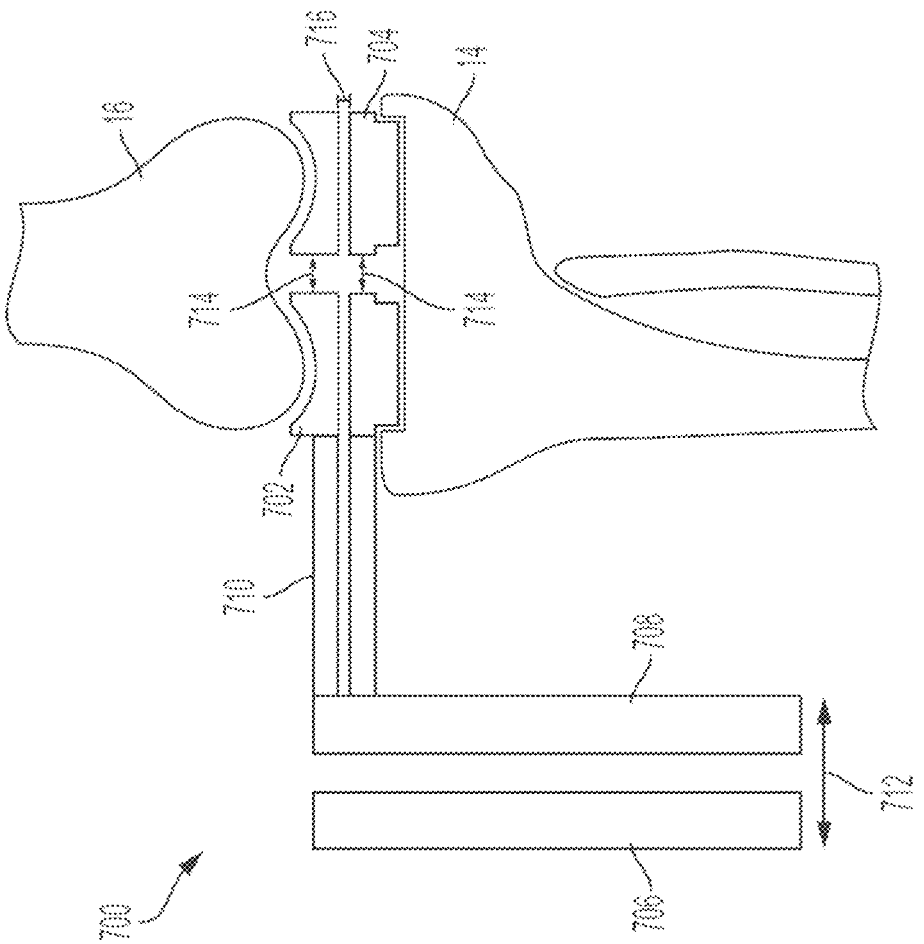
FIG. 17 is a front perspective view of a balancer according to another embodiment of the present disclosure.

FIG. 17 shows a balancer 700 according to another embodiment of the present disclosure. Balancer 700 is a fully adjustable tibial spacer and balancer that allows for trialing of a tibial spacer during a TKA procedure. Balancer 700 is similar to balancer 400 but is fully adjustable requiring no tibial trials or trial inserts for trialing of a tibial spacer. Balancer 700 includes a first post 706 and a second post 708 that can be adjusted to vary the distance between them as indicated by a distance 712 in FIG. 17. Adjusting the distance between the first and second posts allows for adjusting the spacing between medial and lateral femoral plates 702 and medial and lateral tibial plates 704 by a distance 714. An operator can adjust the size of the tibial insert by varying distance 712, which will in turn change the distance between femoral plates 702 and tibial plates 704 via a link 710. Thus, femoral and tibial plate sizes can be increased or decreased by manipulating first post 706 and second post 708 of balancer 700. While distance 714 between femoral plates 702 and tibial plates 704 are simultaneously varied by adjusting distance 712 in this embodiment, in another embodiment distance between the femoral plates and the tibial plates can be individually controlled and adjusted.

A distance 716 between femoral plates 702 and tibial plates 704 of balancer 700 is also adjustable. Depending on the required thickness of the tibial insert, an operator can increase or decrease distance 716 to increase or decrease the thickness of femoral and tibial plates of 700. Thus, balancer 700 provides a fully adjustable tibial inserter allowing an operator to increase the size and thickness of a tibial insert without requiring the need for any tibial inserts. While a typical surgical kit to perform a TKA may include as many as 576 different tibial inserts with different sizes, thickness and procedure-specific configurations, balancer 700 can be utilized without any tibial inserts as balancer 700 is fully adjustable to assume the shape, size and configuration of any required tibial insert.

While a TKA procedure is generally described in these embodiments, the apparatus and methods of the present disclosure can be used for various other knee and hip procedures or any part of these procedures. The various components of tensor 10 and balancer 400 can be modular. For example, the housing of tensor 10 can be configured to couple with femoral and tibial paddles of various sizes. Tensors and balancers disclosed herein can be made wholly, or in part, by polymers such as PEEK, carbon fiber reinforced PEEK, PAEK, UHMWPE, metals, ceramics, combinations of the foregoing, or other suitable materials that are biocompatible and possess sufficient strength and rigidity. Near net shape casting, subtractive manufacturing techniques, and additive manufacturing techniques such as 3D printing may be used to fabricate the tensor and balancers of the present disclosure.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the claims below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. An apparatus for performing an orthopedic procedure on a knee, comprising:

a medial femoral plate and a lateral femoral plate, the medial femoral plate including medial concave articular surface configured to engage a medial condyle of a femur, the lateral femoral plate including a lateral concave articulate surface to engage a lateral condyle of the femur;

a medial tibial plate and a lateral tibial plate;

a first post coupled to the medial femoral plate and the medial tibial plate;

a second post coupled to the lateral femoral plate and the lateral tibial plate;

a link connecting the first post to the second post, and an adjustment mechanism configured to vary a first distance between the first and second posts, and a second distance between the medial femoral plate and the medial tibial plate, wherein the first and second posts are adjustable to vary both medial-lateral and proximal-distal spacing between the femoral and tibial plates.

2. The apparatus of claim 1, wherein the adjustment mechanism includes a rack and pinion system configured to translate the first and second posts relative to each other.

3. The apparatus of claim 1, wherein the link is a telescoping member configured to allow linear translation between the first post and the second post.

4. The apparatus of claim 1, further including a load sensor disposed between at least one of the femoral plates and the tibial plates to measure a load.

5. The apparatus of claim 1, wherein the medial and lateral tibial plates each include a concave articular surface.

6. The apparatus of claim 1, wherein the medial and lateral tibial plates are configured to engage a proximal surface of a tibia.

7. The apparatus of claim 1, further including a sensor array configured to provide real-time data on knee joint alignment and load distribution.

8. The apparatus of claim 1, further including a housing coupled to the first and second posts.

9. The apparatus of claim 1, wherein the medial femoral plate and the lateral femoral plate are configured to be inserted into a knee joint in an anterior-to-posterior direction without everting a patella.

* * * * *